(12) United States Patent
Ferro et al.

(10) Patent No.: US 10,485,721 B2
(45) Date of Patent: Nov. 26, 2019

(54) SURGICAL LEG POSITIONER

(71) Applicant: AOD Holdings, LLC, Arroyo Grande, CA (US)

(72) Inventors: Thomas D Ferro, Arroyo Grande, CA (US); Austin T Ferro, Arroyo Grande, CA (US); Donald J Lee, San Luis Obispo, CA (US); Joseph Phillips, Paso Robles, CA (US)

(73) Assignee: AOD HOLDINGS, LLC, Arroyo Grande, CA (US)

( * ) Notice: Subject to any disclaimer, the term of this patent is extended or adjusted under 35 U.S.C. 154(b) by 969 days.

(21) Appl. No.: 14/878,920

(22) Filed: Oct. 8, 2015

(65) Prior Publication Data

US 2016/0151224 A1 Jun. 2, 2016

Related U.S. Application Data

(63) Continuation-in-part of application No. 14/668,877, filed on Mar. 25, 2015.
(Continued)

(51) Int. Cl.
*A61G 13/00* (2006.01)
*A61G 13/12* (2006.01)
(Continued)

(52) U.S. Cl.
CPC ........ *A61G 13/1245* (2013.01); *A61F 5/3769* (2013.01); *A61G 13/0036* (2013.01);
(Continued)

(58) Field of Classification Search
CPC ........ A61F 5/37; A61F 5/3761; A61F 5/3769; A61F 5/3792; A61G 13/10; A61G 13/12;
(Continued)

(56) References Cited

U.S. PATENT DOCUMENTS 4,181,297 A   1/1980 Nichols
4,299,213 A   11/1981 Violet
(Continued)

OTHER PUBLICATIONS

Imp Innovative Medical Products, Inc. A Global Leader in Patient Positioning http://www.innovativemedical.com/products/DeMayo_UnivDistractor.html, 2015.

*Primary Examiner* — Keri J Nelson
*Assistant Examiner* — Adam Baker
(74) *Attorney, Agent, or Firm* — Cislo & Thomas, LLP

(57) ABSTRACT

A surgical leg positioner capable of bending the knee in varus or valgus while simultaneously distracting the tibia from the femur, the leg positioner having a thigh clamp module, a swing arm module connected to the thigh clamp module in a manner that offsets a joint axis laterally to the side of the knee of the patient so as not to damage the opposite compartment of the knee when bent in varus or valgus, and a rail lock assembly to lock the knee in varus or valgus. The swing arm module also distracts the knee simultaneously when the knee is bent in varus or valgus. The swing arm module also permits flexion and extension of the knee at the knee's natural flexion-extension axis. The surgical leg positioner also utilizes a thigh brace that properly aligns the leg on the surgical leg positioner.

13 Claims, 19 Drawing Sheets

Related U.S. Application Data

(60) Provisional application No. 62/085,311, filed on Nov. 27, 2014.

(51) Int. Cl.
*A61G 13/10* (2006.01)
*A61F 5/37* (2006.01)

(52) U.S. Cl.
CPC ......... *A61G 13/101* (2013.01); *A61G 13/125* (2013.01); *A61G 13/129* (2013.01); *A61G 13/1295* (2013.01)

(58) Field of Classification Search
CPC ............ A61G 13/1235; A61G 13/1245; A61G 13/1285; A61G 13/129; A61G 13/101; A61G 13/1205–13/1255; A61G 13/128; A61G 13/0036; A61G 13/0063; A61G 2200/32; A61G 7/065; A61G 7/075; A61G 7/0755; A61G 7/1082; A61G 7/1096; A61G 7/109; A61G 2210/10
USPC .... 128/845, 846, 878, 881, 882; 5/621, 624, 5/648, 649
See application file for complete search history.

(56) References Cited

U.S. PATENT DOCUMENTS

| | | | |
|---|---|---|---|
| 4,373,709 A | 2/1983 | Whitt | |
| 4,407,277 A | 10/1983 | Ellison | |
| 4,457,302 A | 7/1984 | Caspari et al. | |
| 4,526,165 A | 7/1985 | Mielnik, Jr. et al. | |
| 4,526,355 A * | 7/1985 | Moore | A61G 13/0063 5/624 |
| 4,549,540 A | 10/1985 | Caspari et al. | |
| 4,573,482 A | 3/1986 | Williams, Jr. | |
| 4,766,891 A | 8/1988 | Schultz | |
| 4,886,258 A | 12/1989 | Scott | |
| 4,913,413 A * | 4/1990 | Raab | A61G 13/12 5/624 |
| 5,065,535 A | 11/1991 | Gill et al. | |
| 5,290,220 A | 3/1994 | Guhl | |
| 5,356,100 A | 10/1994 | Bookwalter et al. | |
| 5,395,303 A | 3/1995 | Bonutti et al. | |
| 5,520,627 A | 5/1996 | Maiewicz | |
| 5,645,079 A | 7/1997 | Zahiri et al. | |
| 6,012,456 A | 1/2000 | Schuerch | |
| 7,255,708 B2 * | 8/2007 | Kim | A61H 1/008 128/845 |
| 7,380,299 B1 | 6/2008 | DeMayo | |
| 7,608,074 B2 | 10/2009 | Austin et al. | |
| 7,665,167 B2 | 2/2010 | Branch et al. | |
| 7,832,401 B2 | 11/2010 | Torrie et al. | |
| 7,947,003 B2 | 5/2011 | Bonnefin et al. | |
| 7,947,006 B2 | 5/2011 | Torrie et al. | |
| 7,947,862 B2 | 5/2011 | Livorsi | |
| 7,985,227 B2 | 7/2011 | Branch et al. | |
| 8,048,082 B1 | 11/2011 | DeMayo | |
| 8,052,629 B2 | 11/2011 | Smith et al. | |
| 8,273,043 B2 | 9/2012 | Bonutti et al. | |
| 8,302,228 B2 | 11/2012 | Aboujeoude | |
| 8,721,578 B2 | 5/2014 | Gaylord | |
| 8,840,570 B2 | 9/2014 | Branch et al. | |
| 8,888,718 B2 | 11/2014 | Siston et al. | |
| 9,022,334 B1 * | 5/2015 | DeMayo | F16M 13/022 248/229.22 |
| 2005/0278851 A1 * | 12/2005 | DeMayo | A61G 13/10 5/624 |
| 2008/0097269 A1 | 4/2008 | Weinberg et al. | |
| 2009/0293884 A1 * | 12/2009 | DaSilva | A61G 13/12 128/845 |
| 2012/0046540 A1 | 2/2012 | Branch et al. | |
| 2012/0233782 A1 | 9/2012 | Kreuzer et al. | |
| 2012/0318278 A1 | 12/2012 | Aboujaoude et al. | |
| 2013/0191995 A1 * | 8/2013 | Bellows | A61G 13/0036 5/624 |
| 2014/0101851 A1 | 4/2014 | Schuerch | |
| 2014/0358042 A1 | 12/2014 | Branch et al. | |
| 2015/0231013 A1 * | 8/2015 | Bernardoni | A61F 5/3769 128/845 |

* cited by examiner

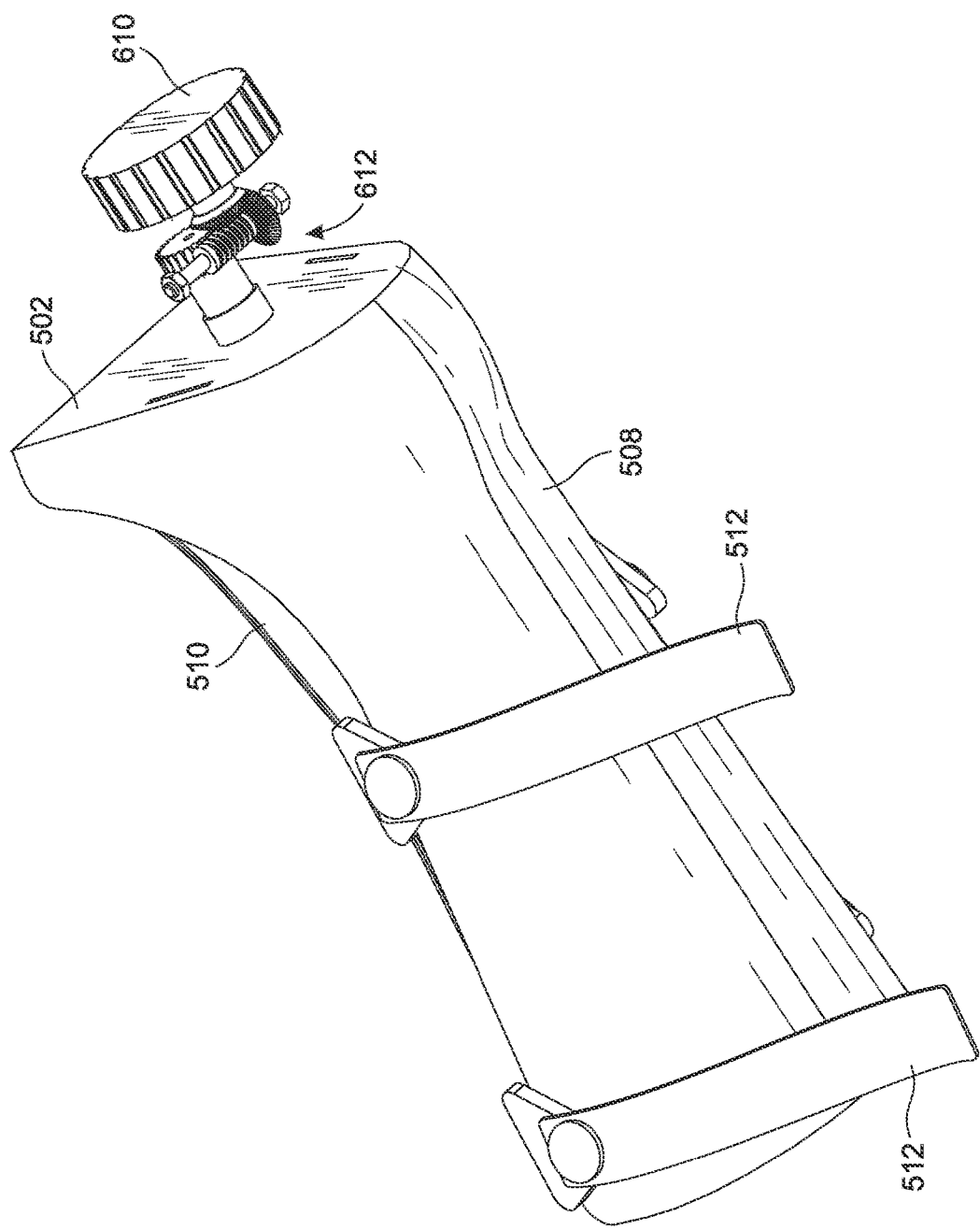

SURGICAL LEG POSITIONER

CROSS-REFERENCE TO RELATED APPLICATION

This patent application is a continuation-in-part of U.S. patent application Ser. No. 14/668,877, filed Mar. 25, 2015, which claims the benefit of U.S. Provisional Patent Application Ser. No. 62/085,311, entitled "Surgical Leg Positioner," filed Nov. 27, 2014, which applications are incorporated in their entirety here by this reference.

TECHNICAL FIELD

This invention relates to a device for holding the leg during a surgery.

BACKGROUND

The restricted space between the femur and tibia in the knee joint limits the accessibility of arthroscopic instruments during knee arthroscopy. The surgeon has to place the patient's knee in specific positions to increase accessibility for surgical procedures. In some cases, the surgeon has to physically hold the knee in positions requiring a significant amount of physical exertion resulting in potential damage to the opposing compartment of the patient's knee joint and potential injury to the surgeon. Damage to the knee joint can occur because the knee compartment opposing the exposed compartment may act as a fulcrum during bending.

Currently, there are leg positioner solutions to take the strain off the surgeons. However, the existing solutions do not address the issue of damaging the opposing compartment of the patient's knee joint. For example, current devices allow bending the knee in varus or valgus to expose the space between the femur and tibia by bracing the opposing compartment of the knee against a barricade and then applying a lateral force. This technique, however, risks damaging the opposing compartment of the knee that acts as the fulcrum/point of leverage. In other devices, the femur and the tibia are linearly distracted. This, however, does not allow the surgeon to be in an optimal position for the surgery. Surgeons prefer having the leg relatively straight and to the side of their body.

For the foregoing reasons there is a need for a surgical knee positioner that does not increase the susceptibility to damage on the opposite compartment of the knee, and yet still allows the leg to be in an optimal position for surgery.

SUMMARY

The present invention is directed to a surgical knee positioner that allows for optimal exposure of the space between the tibia and the femur while placing the leg in the optimal position for surgery for the surgeon, without increasing the damage to the opposing compartment of the knee created by traditional devices.

The present invention is a surgical leg positioner that that allows the leg to bend in varus or valgus (varus/valgus) while simultaneously creating a linear distraction to reduce the risk of damaging the opposing compartment. In some embodiments, this is accomplished by shifting the pivot point laterally far enough to be outside the area of the knee joint so that the opposing compartment does not serve as a fulcrum or pivot point. Rather, by moving the pivot point sufficiently lateral to the knee, the tibia is linearly distracted simultaneously when bending the knee in varus/valgus. In some embodiments, this is accomplished by linearly distracting the tibia from the femur automatically, when bending the knee in varus/valgus.

The invention herein will attach to conventional arthroscopic surgical beds/tables. An object of the invention is to have a component that allows the surgical leg positioner to be adjustable so as to work with either the right or the left leg. Another object of the invention is to control the amount of flexion/extension the patient's leg experiences. Another object of the invention is to control the amount of varus/valgus the patient's leg experiences. Another object of the invention is to have flexion/extension positioning independently controlled from the varus/valgus positioning and vice versa. Another object of the invention is to uniquely provide varus/valgus positioning of the leg while making sure that the opposite compartment of the exposed compartment of the knee will not act as a fulcrum. Another object of the invention is to automatically position the upper leg properly.

BRIEF DESCRIPTION OF DRAWINGS

FIG. 5B is the foot brace shown in FIG. 5A with portions removed to reveal the gear mechanism.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The present invention is directed towards a surgical leg positioner 10 that allows the surgeon to place the knee in an optimal position for surgery, while minimizing the potential damage to the knee by moving the pivot point from being on the opposite compartment of the knee further laterally beyond the knee. In other words, the pivot point or center of rotation when bending the knee in varus or valgus (varus/valgus) is shifted sufficiently lateral to the knee so that the pivot point is not anywhere on the knee joint, such as the opposite compartment as in traditional devices.

Figure 1A:
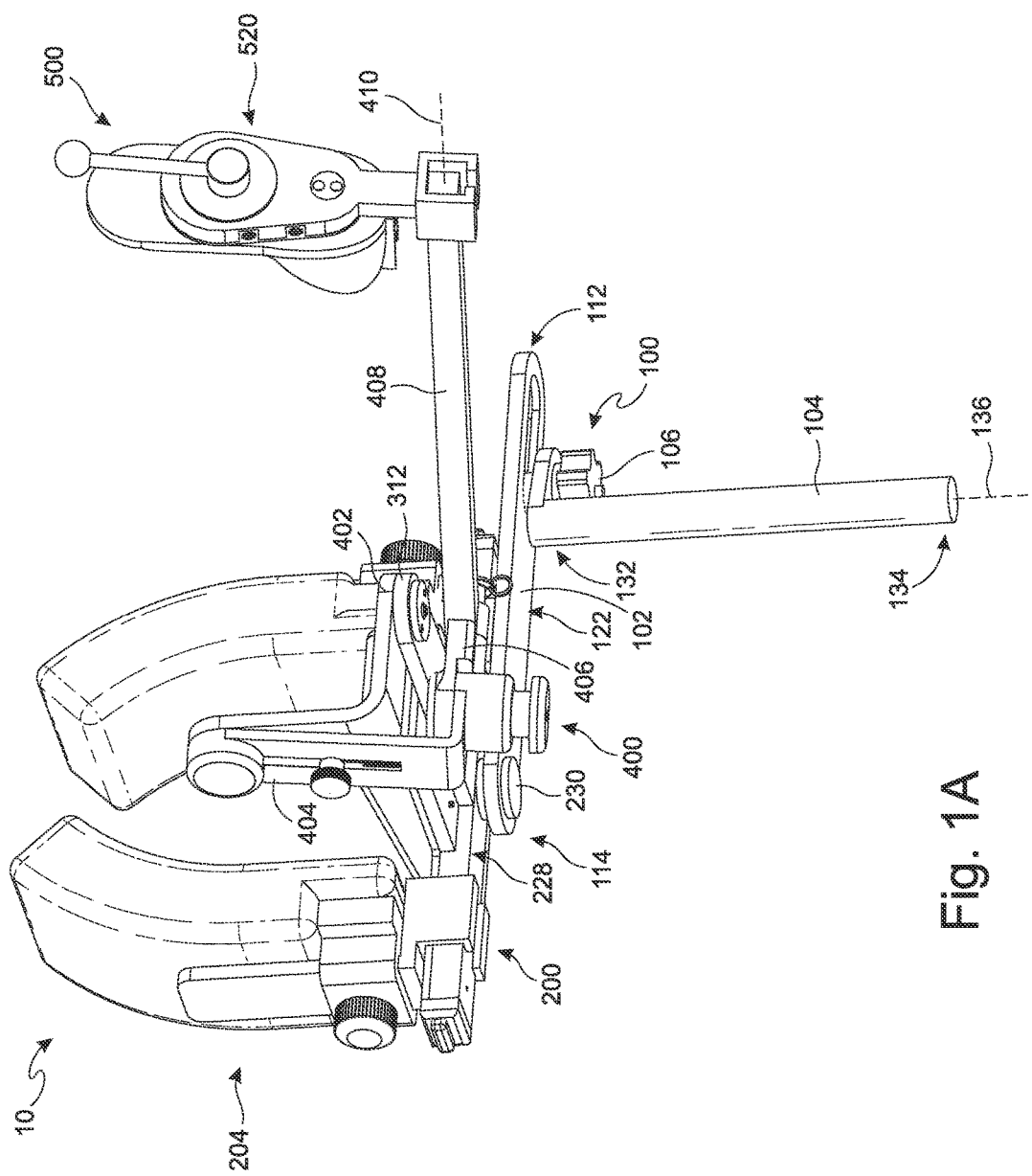
FIG. 1A shows a perspective view from the bottom of an embodiment of the present invention.
Figure 1B:
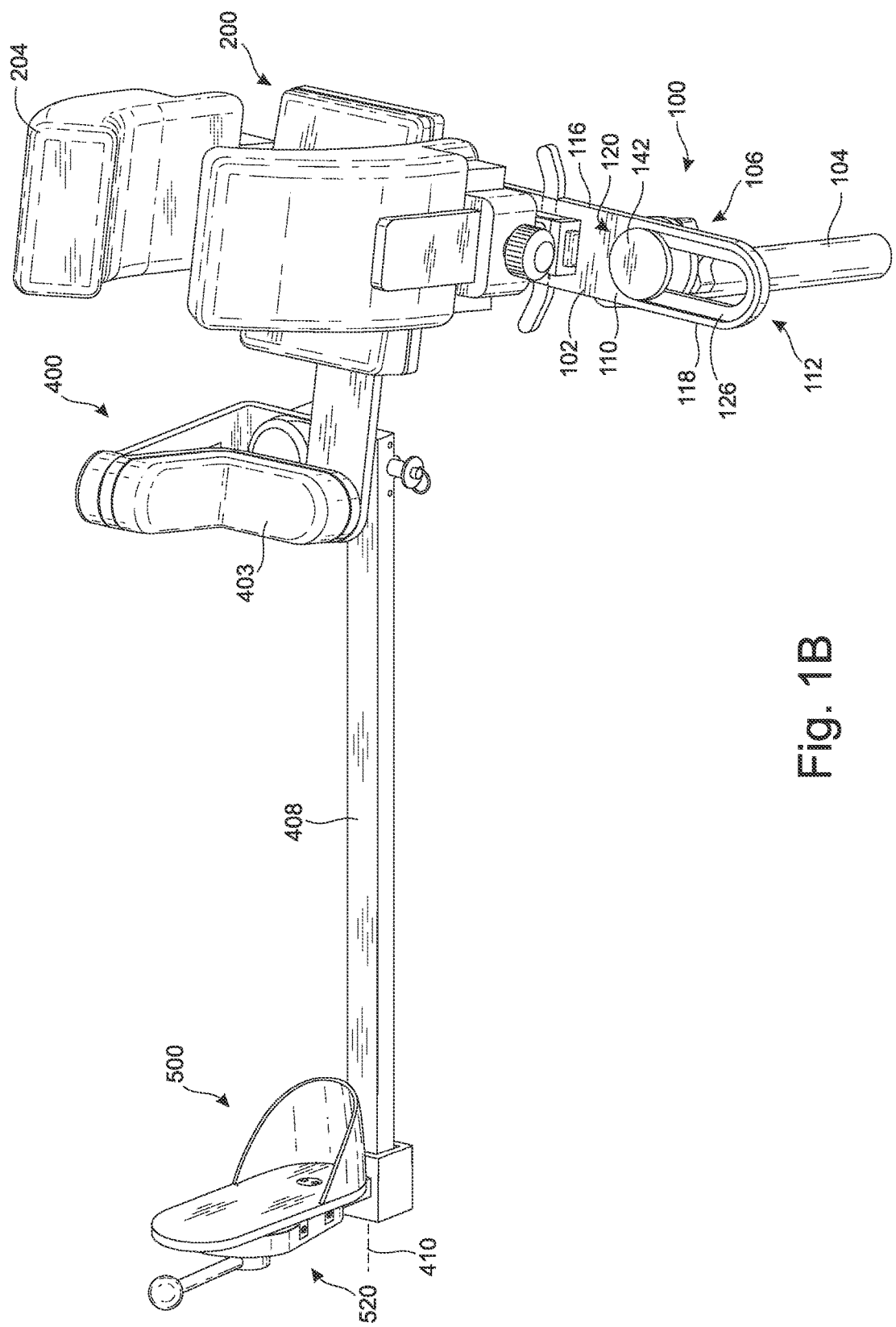
FIG. 1B shows a perspective view from the top of an embodiment of the present invention.
Figure 1C:
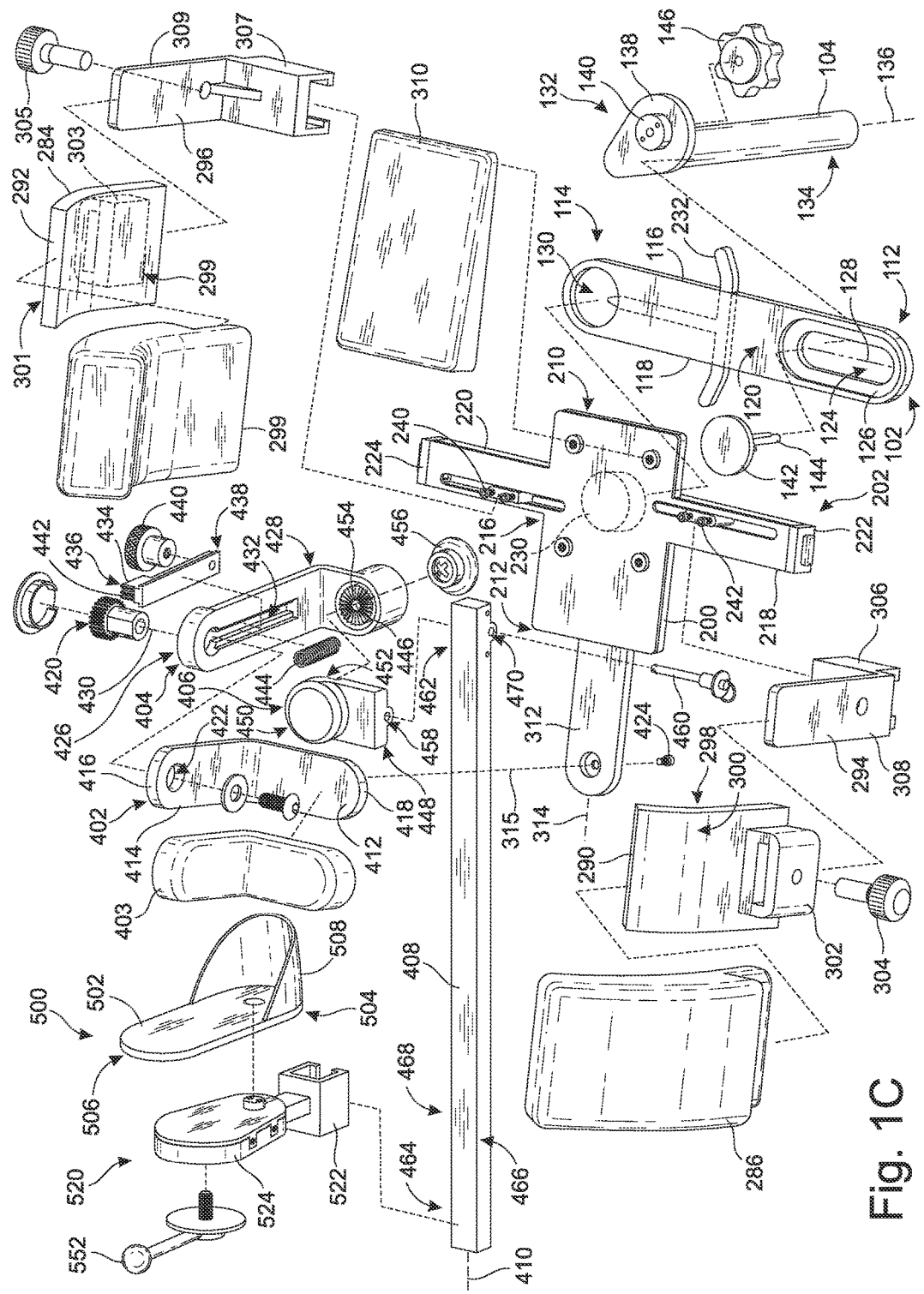
FIG. 1C is a perspective exploded view of an embodiment of the present invention.
Figure 1D:
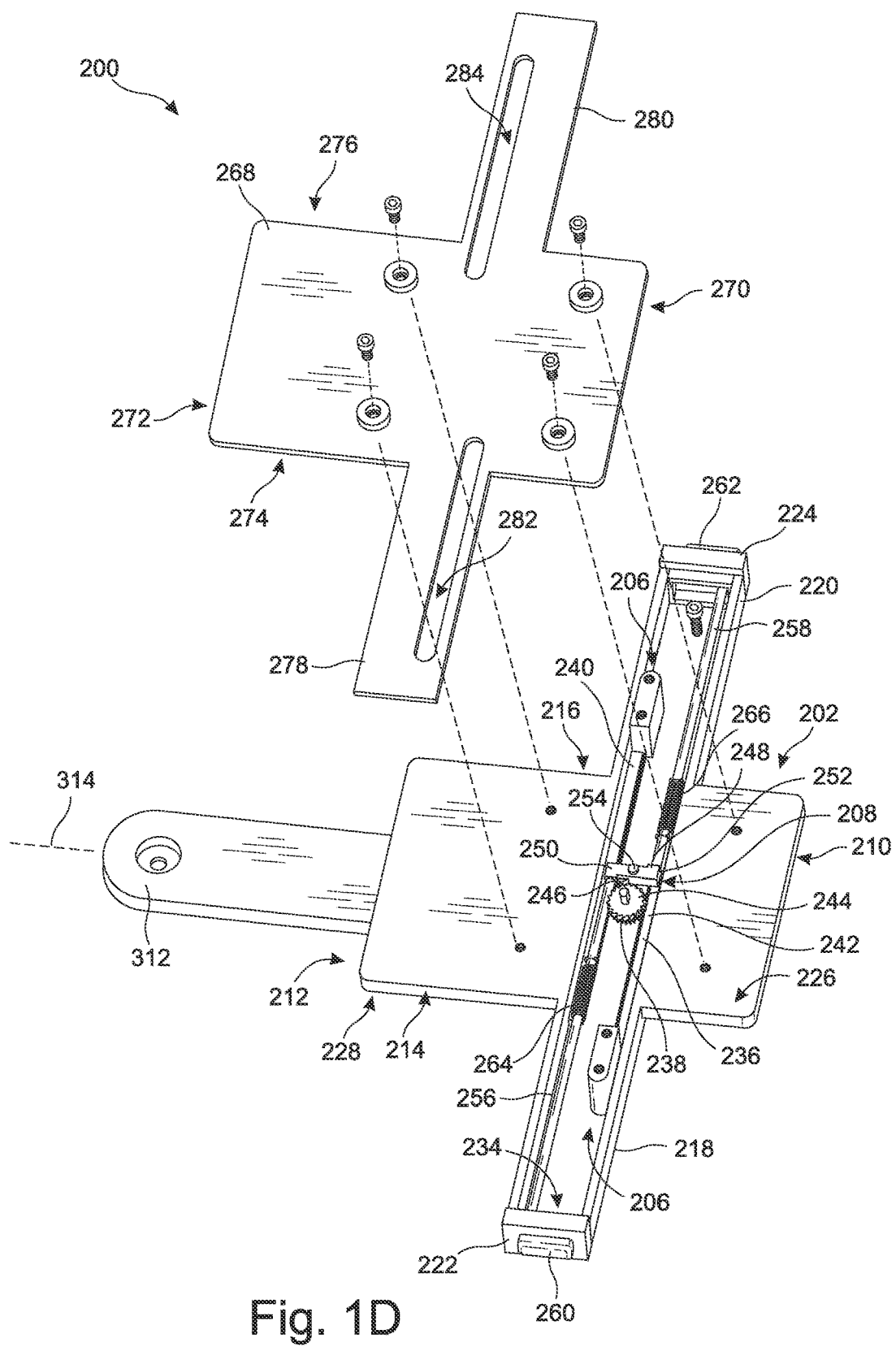
FIG. 1D is a partially exploded view of the thigh clamp module.

As shown in FIGS. 1A-1C, an embodiment of the present invention comprises a surgical bed clamp 100 to attach the leg positioner 10 to a surgical table, a thigh clamp module 200 connected to the surgical bed clamp 100 for supporting the leg, a swing arm module 400 connected to the thigh clamp module 200 that allows proper positioning of the lower leg, and a foot brace 500 to secure the lower leg and foot during manipulation. In some embodiments, the foot brace 500 may further comprise a rotation lock assembly 520 operatively connected to the foot brace 500 to rotate the foot and/or the lower leg to a desired position.

The surgical bed clamp 100 provides a quick and easy way to connect the leg positioner 10 to a surgical table in an adjustable manner. In some embodiments, the surgical bed clamp 100 comprises a supporting member 102, a post 104, and a lock 106. The supporting member 102 may be an elongated plate 110 having a first end 112, a second end 114 opposite the first end 112, and a pair of opposing sides 116, 118. The first end 112, second end 114, and sides 116, 118 define a top surface 120 and a bottom surface 122. The elongated plate 110 may comprise a slot 124. In the preferred embodiment, the first end 112 comprises a recessed surface 126 defining the slot 124. The slot 124 is generally elongated and defines a longitudinal slot axis 128 parallel to the sides 116, 118.

The second end 114 may comprise an opening 130 to attach to the thigh clamp module 200. The second end 114 may be attached to the thigh clamp module 200 in a rotatable manner. In the preferred embodiment, the second end 114 of the supporting member 102 may comprise a circular opening 130 used in connecting with the thigh clamp module 200 in a rotatable manner.

The post 104 is configured to support the supporting member 102 and allow the supporting member 102 to slide in a lateral-medial direction for proper positioning of the patient on the surgical table. In the preferred embodiment, the post 104 may be an elongated rod having a first end 132 and a second end 134 opposite the first end 132, the post 104 defining a longitudinal post axis 136 through the first and second ends 132, 134. The post 104 mounts on to a surgical table in a height adjustable manner by being able to slide up and down within a mount on the surgical table, and being locked in place with pins, clamps, and the like.

The first end 132 may comprise a platform 138 defined in a plane perpendicular to the longitudinal post axis 136 of the elongated post 104. The platform 138 may comprise a shaft 140 projecting perpendicularly upward, parallel to the elongated post 104. The shaft 140 projects through the slot 124 of the supporting member 102, and the platform 138 abuts against the bottom 122 of the supporting member 102. This configuration allows the shaft 140 to slide within the slot 124 in the lateral-medial direction.

A lock 106 may be used to lock the supporting member 102 in place relative to the elongated post 104. In the preferred embodiment, the lock 106 may be a compression or resistance lock comprising a flanged head 142 mountable on top of the shaft 140 and seated within the recessed surface 126, a rod 144 projecting downwardly through the shaft 140 and the platform 138, and a knob 146 attached to the rod 144 and configured to compress (tighten) or loosen the flanged head 142 against the recessed surface 126 to lock the supporting member 102 in place or unlock the supporting member 102 to allow it to move laterally within the recessed surface 126, which allows the thigh clamp module 200 to be adjusted.

In another embodiment, the surgical bed clamp 100 comprises a base clamp 900, a vertical post 902 protruding from the base clamp 900, a compression plate 904 attached to the vertical post 902, and a horizontal post 906 perpendicular to the vertical post 902. The compression plate 904 comprises a first plate portion 910, a second plate portion 912, a narrow gap 914 defined therebetween to allow the first plate portion 910 and the second plate portion 912 to be compressed, a compression lock 916 inserted through the compression plate 904 and configured to compress and release the first and second plate portions 910, 912 against each other, and a horizontal channel 918.

Protruding from the horizontal channel 918 of the compression plate 904 is the horizontal post 906 having a first end 920, and a second end 922 opposite the first end 920, wherein the compression plate 904 is mounted adjacent to the first end 920 of the horizontal post 906 and configured to slide along the horizontal post 906 and be clamped along the horizontal post 906.

In some embodiments, to increase the sturdiness of the surgical bed clamp 100, multiple vertical posts 902 and horizontal posts 906 may be used.

The thigh clamp module 200 provides support and security to the upper leg, namely, the femur or thigh. As shown in Figures IC and ID, the thigh clamp module 200 comprises comfortable thigh braces that are adjustable to accommodate legs of any size. The thigh clamp module 200 may be mounted on the surgical bed clamp 100, preferably at the second end 114 of the supporting member 102. The thigh clamp module 200 may be rotatably mounted on the surgical bed clamp 100 for additional adjustment. In the preferred embodiment, the thigh clamp module 200 comprises a base frame 202, a thigh brace 204 mounted on the base frame 202 to hold the thigh, an adjuster 206 housed in the base frame 202 to adjust the sizing of the thigh brace 204, and a brace lock assembly 208 to lock the adjuster 206 in place.

The base frame 202 comprises a proximal end 210, a distal end 212 opposite the proximal end 210, a pair of opposing side ends 214, 216 adjacent to the distal end 212 and the proximal end 210, a pair of lateral extensions 218, 220 projecting laterally away from each other from their respective side ends 214, 216, each lateral extension 218, 220 terminating at a lateral free end 222, 224. The proximal end 210, distal end 212, and opposing side ends 214, 216, and lateral extensions 218, 220 define a top surface 226 and a bottom surface 228 opposite the top surface 226.

The bottom surface 228 may comprise a rotation mount 230. The rotation mount 230 may be seated in the circular opening 130 at the second end 114 of the elongated plate 110. The elongated plate 110 may further comprise a rotation mount lock to prevent rotation of the thigh clamp module 200 about the rotation mount 230. The rotation mount lock 232 may be a structure that wedges or embeds itself into the rotation mount 230 or creates any other kind of resistance to stop any rotation.

The top surface 226 comprises a lateral channel 234. In the preferred embodiment, the lateral channel 234 extends substantially from the lateral free end 222 of one lateral extension 218 to the lateral free end 224 of the second lateral extension 220.

Housed within the lateral channel 234 is the adjuster 206. The adjuster 206 allows the thigh brace 204 to move or adjust laterally in order to accommodate legs of different sizes. In the preferred embodiment, the adjuster 206 may be a rack and pinion assembly 236, although any sliding mechanism can be used. The rack and pinion assembly 236 comprises a pinion 238 centrally located in the lateral channel 234, a first rack 240 operatively connected to and positioned on one side of the pinion 238, and a second rack 242 operatively connected to the pinion 238 on the diametrically opposite side of the pinion 238. The two racks 240, 242 slide laterally relative to each other. Due to the dual rack and single pinion configuration, movement of the two racks are synchronized and centered about the pinion, thereby, ensuring proper alignment of the leg on the base frame. Thus, as the patient is being secured in the surgical leg positioner 10, the patient's leg is automatically being properly aligned as the thigh brace automatically centers itself on the base frame 202.

A brace lock assembly 208 can be used to lock the adjuster 206 to fix the thigh brace 204 at a desired size by locking the sliding mechanism, such as the rack and pinion assembly 236, at a desired location. In the preferred embodiment, the brace lock assembly 208 comprises a ratchet 244 fixedly mounted on the pinion 238 to rotate with the pinion 238, a pawl 246 operatively connected to the ratchet 244 to permit rotation of the ratchet 244 in one direction, a trigger 248 connected to the pawl 246, the trigger 248 having a first end 250 and a second end 252 opposite the first end 250 and a mounting pin 254 therebetween with a first trigger rod 256 attached to the trigger 248 at the first end 250 and extending perpendicularly away from the trigger 248 in a first direction, a second trigger rod 258 attached to the trigger 248 at the second end 252 and extending perpendicularly away from the trigger 248 in a second direction opposite of the first direction, a first trigger button 260 attached to the first trigger rod 256, and a second trigger button 262 attached to the second trigger rod 258. Depression of the first trigger button 260 or the second trigger button 262 causes the trigger 248 to rotate about the mounting pin 254 and disengage from the ratchet 244 allowing the racks 240, 242 to slide along the channel 234. A first spring 264 may be operatively connected to the first trigger rod 256 and a second spring 266 may be operatively connected to the second trigger rod 258, the first and second springs 264, 266 imparting a laterally, outwardly biasing force against the first and second trigger rods 256, 258, respectively, causing the pawl 246 to engage the ratchet 244 in its natural state.

In some embodiments, a flat base frame cap 268 may be used to cover the adjuster 206. The base frame cap 268 may comprise a proximal end 270, a distal end 272 opposite the proximal end 270, a pair of opposing side ends 274, 276 adjacent to the distal end 272 and the proximal end 270, and a pair of guide arms 278, 280 projecting laterally away from each other from their respective side ends 274, 276 to cover their respective lateral extensions 218, 220. Each guide arm 278, 280 comprises a guide arm slot 282, 284. Portions of the adjuster 206, in particular, the racks 240, 242, may protrude through the guide arm slots 282, 284 to attach the adjuster 206 housed inside the base frame 202 with the thigh brace 204 mounted outside and on top of the brace frame 202.

The thigh brace 204 provides comfort while securing the upper leg. In the preferred embodiment, the thigh brace 204 comprises a pair of side pads 286, 288 each side pad mounted on its own side pad frame 290, 292, each side pad frame 290, 292 movably mounted on a pad frame bracket 294, 296. Each side pad frame 290, 292 is defined by an interior face 298, 299 and an exterior face 300, 301, each exterior face 300, 301 comprising an exterior slot 302, 303 and a tightening bolt 304, 305. Each pad frame bracket 294, 296 comprises a sliding bracket 306, 307 and a support arm 308, 309. Each exterior slot 302, 303 is configured to slide along their respective support arms 308, 309 and the tightening bolts 304, 305 are configured to tighten their respective side pad frames 290, 292 at any point along their respective support arms 308, 309. Each sliding bracket 306, 307 is attachable to its respective rack 240, 242 through their respective guide arm slots 282, 284 on their respective guide arms 278, 280. A base pad 310 may be mounted on the base frame 202 to accommodate the bottom of the thigh. The side pads 286, 288 and the base pad 310 are made of cushioning material for comfort.

A distal extension 312 may project away from the distal end 212 and away from the proximal end 210 of the base frame 202. The distal extension 312 may be used to attach the thigh clamp module 200 to the swing arm module 400. The longitudinal center line of the distal extension 312 defines the main axis 314 of the surgical leg positioner 10.

The swing arm module 400 provides the improved ability for the leg positioner to distract the tibia from the femur while simultaneously bending the need in varus/valgus. The swing arm module 400 is attached to the thigh clamp module 200. In the preferred embodiment, the swing arm module 400 is attached to the distal extension 312 and comprises a base arm 402 connecting the swing arm module 400 to the thigh clamp module 200, a vertical bracket 404 attached to the base arm 402 to allow for flexion and extension at the knee, a horizontal bracket 406 attached to the vertical bracket 404 for bending the knee in varus/valgus, and a main axle or rail 408 attached to the horizontal bracket 406 to support the lower leg. The term rail and axle are intended to mean the same thing (essentially an elongated bar on which other components of the invention can be attached) and may be used interchangeably with respect to the surgical leg positioner. The main axle or mail rail 408 defines a main axle axis or main rail axis 410.

In the preferred embodiment, the base arm 402 has an L-shape appearance comprising a horizontal arm 412 and a vertical arm 414. A cushioning pad 403 may be placed on the base arm 402 for comfort under the patient's knee. The vertical arm 414 has a first terminal end 416 and the horizontal arm 412 has a second terminal end 418. The first terminal end 416 comprises a rotating mechanism 420 and rotatably attaches to the vertical bracket 404 at a first joint 422. In the preferred embodiment, the rotating mechanism 420 may be a toothed-gear. The second terminal end 418 at the horizontal arm 412 may be connected to the distal extension 312 of the thigh clamp module 200 in a rotatable manner about a vertical base frame axis 315. This allows the base arm 402 to be moved from one lateral side of the thigh clamp module 200 to the opposite lateral side by rotating the base arm 402 180 degrees about the vertical base frame axis 315. This allows the same surgical leg positioner 10 to be used for the left leg or the right leg, or to bend the knee in varus or valgus. A lock mechanism 424 may be provided to secure the base arm 402 in position once in place. The main axle 408 may have to be temporarily detached from the base arm 402 during the reversal of sides.

The vertical bracket 404 comprises an upper end 426 and a lower end 428 opposite the upper end 426. The upper end 426 may be rotatably attached to the vertical arm 414 of the base arm 402 at the rotating mechanism 420 to allow the vertical bracket 404 to rotate about a first joint axis 430 defined by the rotating mechanism 420. The first joint axis 430 may be perpendicular to the main axis 314.

In the preferred embodiment, the vertical bracket 404 comprises a brake slot 432 through which the rotating mechanism 420 can protrude and connect with the vertical bracket 404. Below the rotating mechanism 420 may be a brake 434 slidably mounted within the slot 432 to lock or unlock the rotating mechanism 420. The brake 434 may have a first end 436, a second end 438 opposite the first end 436, and a handle 440 therebetween. The first end 436 may comprise an engagement surface 442. For example, where the rotating mechanism 420 is a toothed gear, the engagement surface 442 may be a toothed-end, a wedge, or the like to be able to stop the rotation of the toothed gear. Therefore, the user can use the handle to slide the slide brake 434 along the slot 432 to engage or disengage from the rotating mechanism 420. In some embodiments, a spring 444 positioned in the slot 432 abutting the second end 438 may be used to impart a biasing force against the second end 438 causing the engagement surface 442 to engage the rotating mechanism 420 in the natural configuration. Thus, in the natural state, the slide brake 434 is in the locked configuration and the user must overcome the biasing force of the spring 444 to unlock the vertical bracket 404 (e.g., disengage the toothed gear).

When the slide brake 434 is disengaged from the rotating mechanism 420, the vertical bracket 404 is allowed to rotate about the first joint axis 430. The upper end 426 of the vertical bracket 404 is positioned above the main axle 408 so that when the patient's leg is properly positioned in the leg positioner 10, the flexion-extension axis 431 of the knee is substantially in line or co-linear with the first joint axis 430. This prevents unintended distraction and allows flexion and extension to be independent of distraction, unlike prior art devices that place barriers near the popliteal fossa (i.e. behind the knee joint), which inherently causes distraction during flexion of the knee due to the pivot point of the device and the patient's knee not being aligned. Therefore, these prior art devices are potentially dangerous for the patient if the flexion/extension mechanism somehow fails and drops the leg while fully secured into one of the devices. The end result may be harmful damage to the patient's ligaments within the knee caused by unintentional distraction of the knee joint.

In some embodiments, the vertical bracket 404 or the base arm 402 may be adjustable to adjust the height of the rotating mechanism 420 so that the user can position the first joint axis 430 to be substantially co-linear with the flexion-extension axis 431 about which the knee naturally bends. In some embodiments, the height of the rotating mechanism 420 within the brake slot 432 may be adjustable to change the level of the first joint axis 430.

The lower end 428 of the vertical bracket 404 is attachable to the main axle 408 such that the main axle 408 is perpendicular to the vertical bracket 404 and perpendicular to the first joint axis 430. Therefore, when the vertical bracket 404 rotates about the rotating mechanism 420, the lower end 428 of the vertical bracket 404 swings in an arching manner. With main axle 408 projecting perpendicularly therefrom, the main axle 408 moves up and down. Since the main axle 408 supports the lower leg, the lower leg is able to move up and down through its natural flexion/extension movement due to the bending action at the knee.

In order to bend the knee in varus/vagus, the main axle 408 is connected to the vertical bracket 404 by a horizontal bracket 406 located at a second joint that can rotate about a second joint axis 446 that is perpendicular to the main axis 314 and the first joint axis 430. In the preferred embodiment, the horizontal bracket 406 has a medial end 448 and a lateral end 450. The lateral end 450 defines a circular cavity 452 into which a gear plate 454 can be removably seated to rotatably connect to the lower end 428 of the vertical bracket 404. The gear plate 454 is connected to the lower end 428 of the vertical bracket 404 in a manner that does not allow the gear plate 454 to rotate. In some embodiment, the lower end 428 may comprise a pawl that allows the gear plate 454 to move in one direction, but not the other. The surgeon can push on the main axle 408 to cause the main axle 408 to move incrementally away from the surgeon to hold the leg in the proper position in varus or valgus. The gear plate 454 can move axially upwardly and downwardly relative to the lower end 428 of the vertical bracket 404. The gear plate 454 has a locked configuration in which the gear plate 454 is seated within the cavity 452 and engaged with the lateral end 450 to prevent movement of the horizontal bracket 406, and an unlocked configuration in which the gear plate 454 is disengaged from the lateral end 450 to allow the horizontal bracket 406 to rotate about the second joint axis 446. The gear plate 454 may have a knob 456 for engaging and disengaging the gear plate 454. Other mechanisms can be used to control the rotation of the horizontal bracket 406.

This configuration allows the second joint axis 446 to be offset from the main axle axis (main rail axis) 410. With the upper leg secured in the thigh brace 204, and the lower leg secured by the main axle 408 and foot brace 500, the surgeon can bend the knee in varus/valgus while simultaneously separating the femur from the tibia without having to shove the leg against a barrier. In addition, the surgeon may be able to control the proper distance between the center of the knee and the second joint axis 446 so as to control the extent the knee is bent in varus/valgus with the correct amount of distraction. For example, the horizontal bracket 406 may be adjustable or telescoping.

Figure 2:
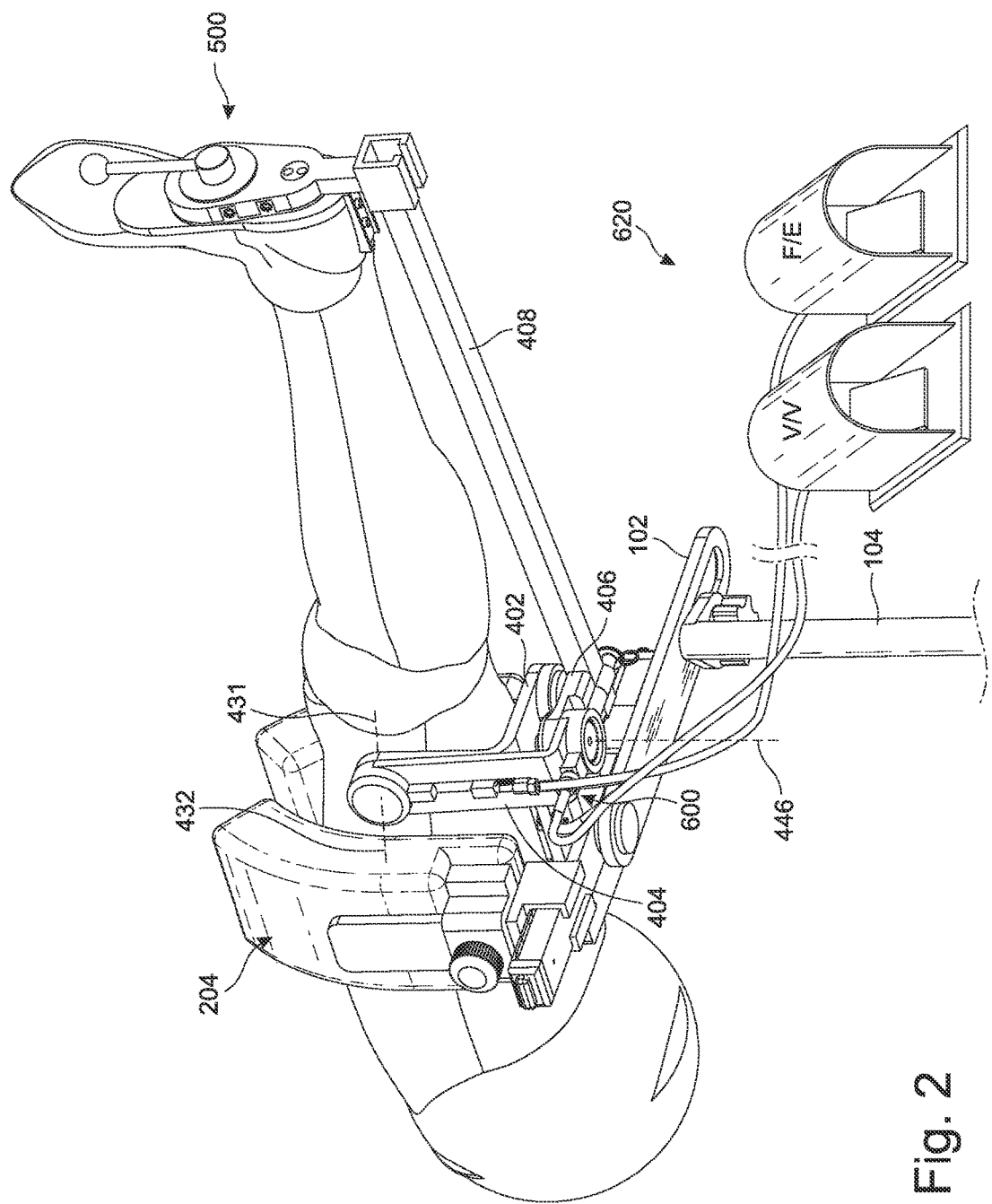
FIG. 2 is a perspective view from the bottom of another embodiment of the present invention with the leg in place.
Figure 3:
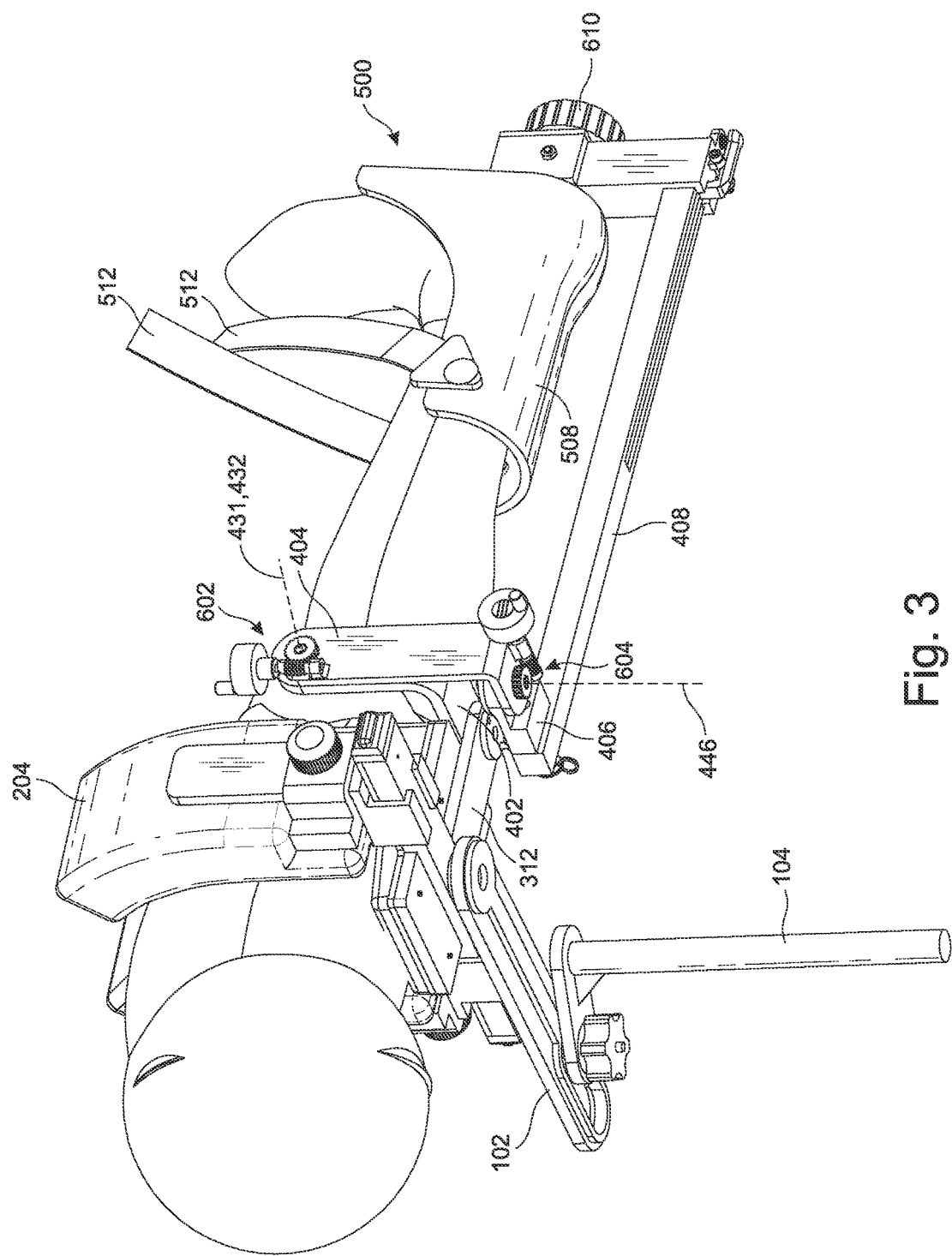
FIG. 3 is a perspective view from the bottom of another embodiment of the present invention with the leg in place.

With the proper orientation of the components as described above, the flexion-extension movement and the varus/valgus movement can be accomplished in a variety of different ways. For example, a series of gear mechanisms can be set up to effectuate the desired movement remotely as shown in FIG. 2. For example, in some embodiments, the gear mechanisms may be controlled 600 so that the movements can be automated. The gear mechanisms may be attached to actuators 620, such as foot pedals, handle actuators, and the like, to allow the surgeon to control with his feet or hands the precise flexion-extension movement (F/E) and the varus/valgus movement (V/V). In some embodiments, the actuators 620 may mechanically actuate cables to lock and release the pawl that engages with the gears for varus/valgus and/or flexion/extension. In some embodiments, the actuators 620 may be electrically controlled, for example, by being operatively connected to a stepper motor to control the gear mechanisms. In some embodiments, the flexion/extension and varus/valgus may be controlled wirelessly using, for example, bluetooth or other radiofrequency communication technology, including voice-command so that the surgeon can simply command with his/her voice the amount and type of movement for the surgical leg positioner to undergo. In some embodiments, as shown in FIG. 3, worm gears 602, 604 may be used for ease of adjustment. Many types of locking mechanisms can be used to secure each component in place, including pins, locks, magnets, electromagnets, mechanical locks, electromechanical locks, and the like.

The horizontal bracket 406 may be reversibly attached to the main axle 408. In addition, the horizontal bracket 406 may be attachable to one side of the main axle 408 or the opposite side of the main axle 408. This interchangeable connection on either side of the main axle 408 allows the main axle 408 to move in one lateral direction relative to the base frame 202 or the opposite lateral direction relative to the base frame 202. This allows the surgical leg positioner 10 to be used for either the left leg or the right leg or to bend the knee in varus or valgus. For example, in the configuration shown in FIG. 1B, the main axle 408 could be bent to the right of the patient, and if the right leg was secured in the leg positioner 10, the right knee could be bent in valgus, whereas if the left leg was secured in the leg positioner 10, the left knee could be bent in varus. However, if the base arm 402 was placed on the opposite side 466 of the main axle 408 and the horizontal bracket 406 connected to the main axle 408 on the other side 466, then the main axle 408 could be bent towards the patient's left side, allowing the left leg to be bent in valgus or the right leg bent in varus. In the preferred embodiment, the medial end 448 comprises a horizontal channel 458 configured to receive a locking pin 460. The locking pin 460 can be removed from the horizontal channel 458, and the horizontal bracket 406 moved to the other side of the main axle 408 and attached thereto with the locking pin 460 from the opposite side.

The main axle 408 has a proximal end 462, a distal end 464 opposite the proximal end 462, a first side 466 adjacent to the proximal end 462 and the distal end 464, and a second side 468 opposite the first side 466 and adjacent to the proximal end 462 and the distal end 464. The proximal end 462 comprises a through-hole 470 extending from the first side 466 to the second side 468. The horizontal channel 458 of the horizontal bracket 406 can be aligned with the through-hole 470 so that the locking pin 460 can be inserted through the through-hole 470 and the horizontal channel 458 to connect the main axle 408 to the horizontal bracket 406.

In some embodiments, as shown in FIG. 6A-8 rather than locking the main rail 408 at the proximal end 462, the main rail 408 may be locked at the distal end 464. In such an embodiment, a fixed rail 700 may be used as an anchor to hold the main rail 408 at various positions. However, the main rail 408 is still rotatably attached to the vertical bracket at a joint that is laterally offset from the main rail axis 410.

Figure 6A:
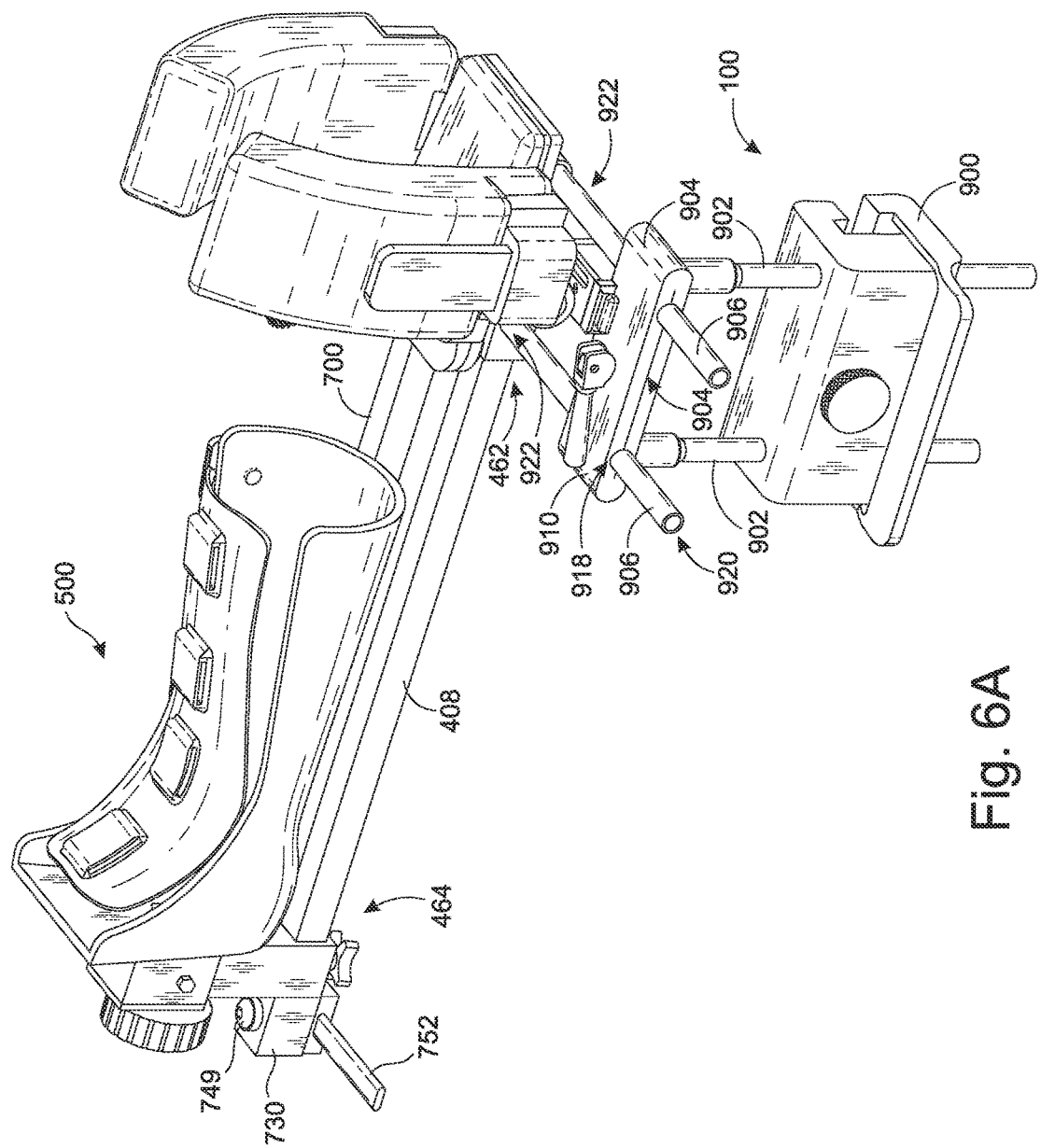
FIG. 6A is a perspective view of another embodiment of the present invention.
Figure 6B:
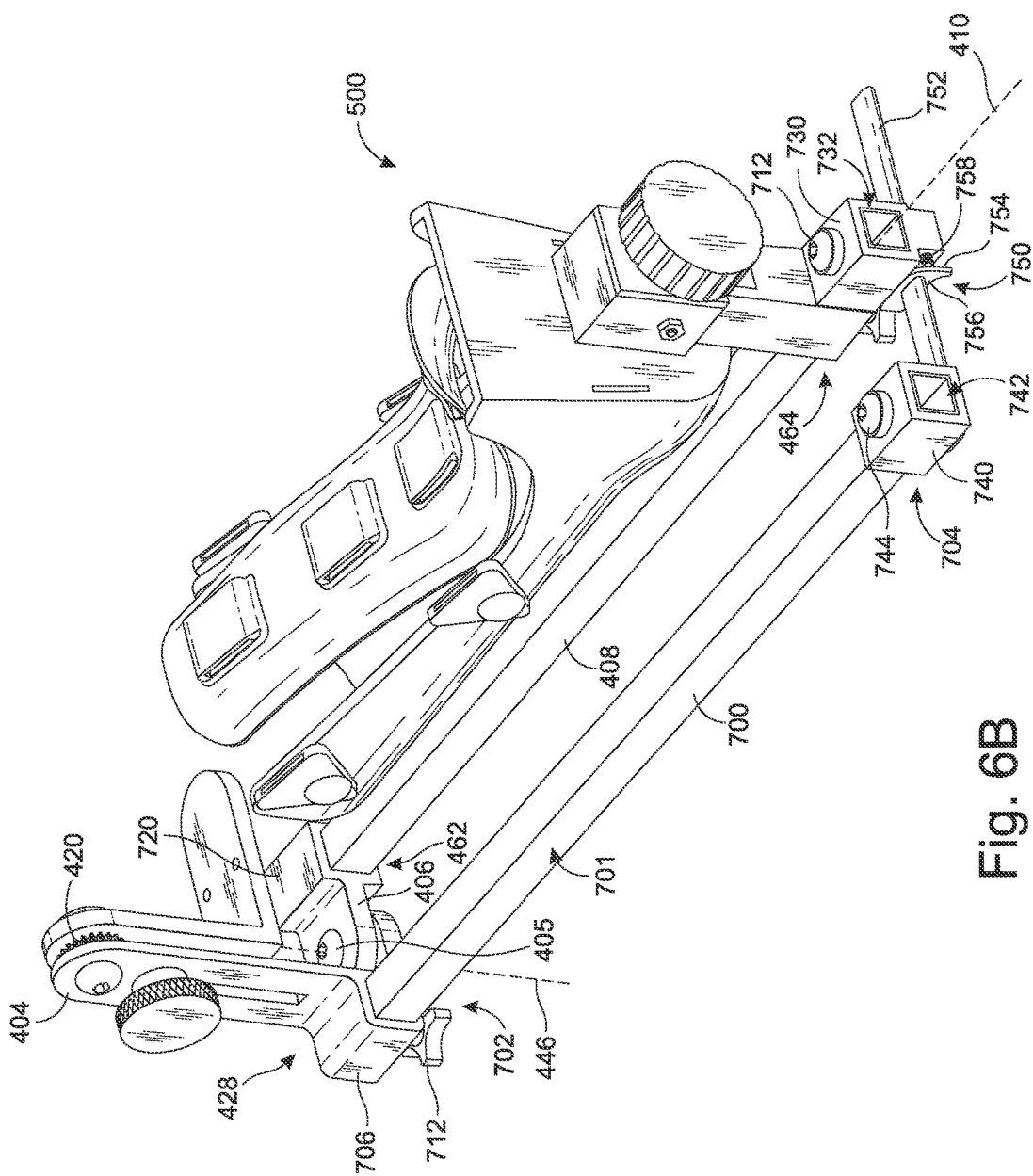
FIG. 6B is another perspective view of the embodiment shown in FIG. 6A, but without the surgical bed clamp and the thigh clamp module shown for the sake of clarity.
Figure 6C:
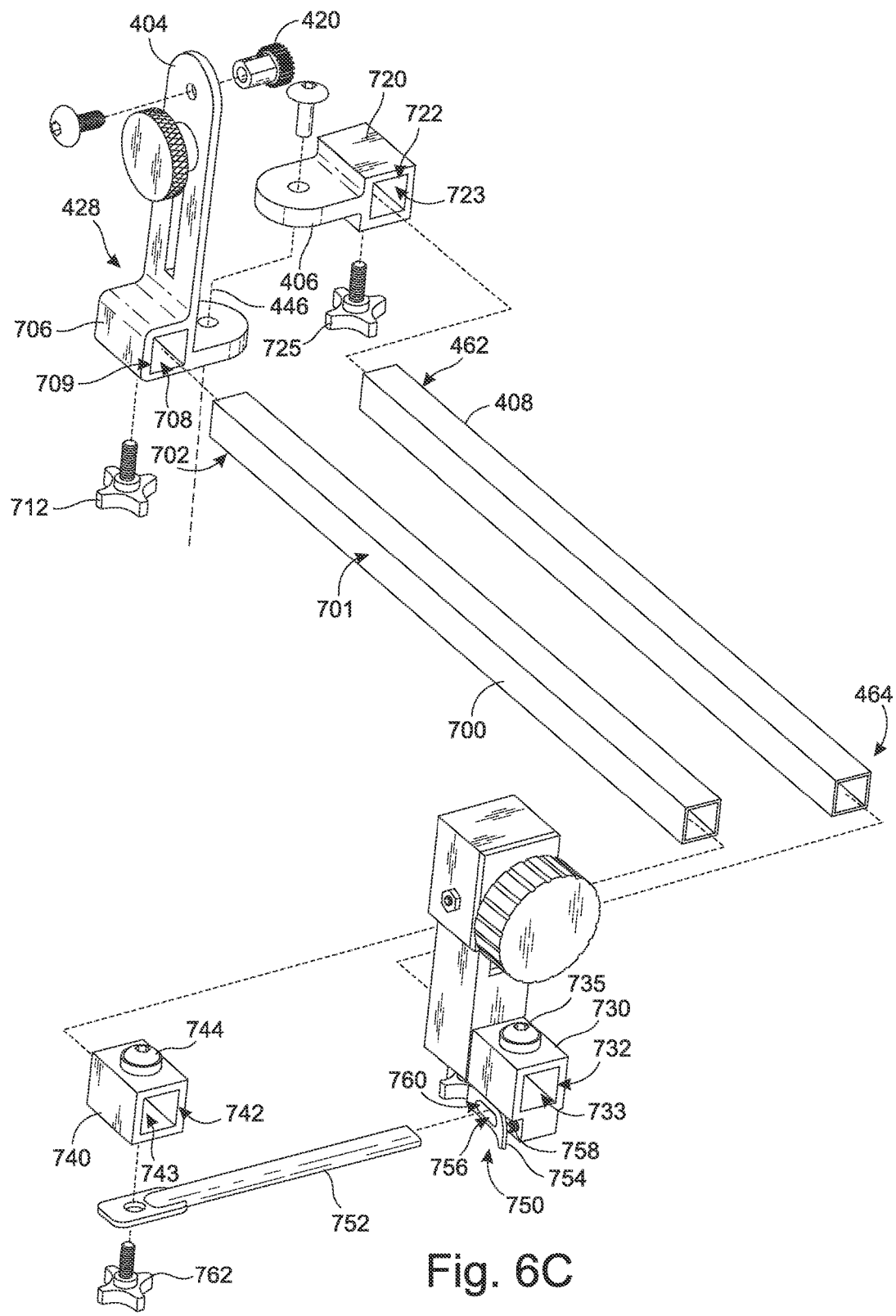
FIG. 6C is an exploded view of the embodiment show in FIG. 6B.

With reference to FIGS. 6B and 6C, the fixed rail 700, like the main rail 408, has a proximal end 702 and a distal end 704. The proximal end 702 of the fixed rail 700 may be attached to the lower end 428 of the vertical bracket 404. The lower end 428 of the vertical bracket 404 may comprise a first rail mount 706 to receive the proximal end 702 of the fixed rail 700. The first rail mount 706 can be any kind of fastening mechanism to secure the proximal end 702 of the fixed rail 700 in place. In the preferred embodiment, the first rail mount 706 defines a first holding channel 708. The first holding channel is defined by an inner wall 709 having dimensions substantially similar to the outer surface 701 of the fixed rail 700. This allows the fixed rail 700 to slide in and out of the first holding channel 708 so as to change the effective length of the fixed rail 700. The first rail mount 706 may comprise a fastening mechanism 712 to fasten the fixed rail 700 at the desired position. For example, the fastening mechanism 712 may be a bolt that gets screwed through a hole in the first rail mount 706 until it abuts against the fixed rail 700. However, other types of connections can be used, such as clamps, bolts, screws, and the like.

The proximal end 462 of the main rail 408 may still be attached to the horizontal bracket 406, which in turn is rotatably attached to the vertical bracket 404. The rotating attachment 405 between the vertical bracket 404 and the horizontal bracket 406 may be a freely rotating attachment. The horizontal bracket 406 may comprise a second rail mount 720 to hold the proximal end 462 of the main rail 408. In the preferred embodiment, the second rail mount 720 may comprise an inner wall 722 that defines a second holding channel 723 through which the proximal end 462 of the main rail 408 can be inserted and, optionally, secured with a fastening mechanism 725 similar to the fastening mechanism 712 for the first rail mount 706. However, other types of connections can be used, such as clamps, bolts, screws, and the like.

The distal end 464 of the main rail 408 may be attached to a third rail mount 730. In the preferred embodiment, the third rail mount 730 comprises an internal wall 732 that defines a third holding channel 733 to allow the distal end 464 of the main rail 408 to slide along the third holding channel 733. A lock 784 secures the third rail mount 730 in place. This allows the user to adjust the distance of the foot brace 500 to the thigh clamp module 200 by sliding the third rail mount 730 to the proper position along the main rail 408. The third rail mount 730 can then be fastened to the main rail 408 to prevent any further longitudinal movement along the main rail 408 with a fastening mechanism 735 like those used for the first and second rail mounts 706, 720, and variations thereof.

This arrangement places the fixed rail 700 adjacent and lateral to the main rail 408 with the proximal end 702 of the fixed rail 700 adjacent to the proximal end 462 of the main rail 408, and the distal end 704 of the fixed rail 700 adjacent to the distal end 464 of the main rail 408. The distal end 704 of the fixed rail 700 may be operatively connected to a fourth rail mount 740. The fourth rail mount 740 may comprise an interior wall 742 that defines a fourth holding channel 743 to slidably receive the fixed rail 700. A fastening mechanism 744, like those used for the previous rail mounts and variations thereof, can be used to secure the fourth rail mount 740 onto the fixed rail 700.

A rail lock assembly 750, may be operatively attached to the distal ends 464, 704 of the main rail 408 and the fixed rail 700. In the preferred embodiment, the rail lock assembly 750 is attached to the third and fourth rail mounts 730, 740. The rail lock assembly 750 allows the distal end 464 of the main rail 408 to be fixed in various lateral positions relative to the fixed rail 700. In other words, since the proximal end 462 of the main rail 408 is rotatably connected to the vertical bracket 404, the distal end 464 of the main rail 408 is allowed to move in an arcuate path laterally towards and away from the fixed rail 700. Since the rotatable connection 405 at the vertical bracket 404 allows for free rotation, meaning it does not have a locking mechanism, the rail lock assembly 750 provides for a new mechanism for locking the main rail 408 in place anywhere along the arcuate path.

In some embodiments, as shown in FIGS. 6B and 6C, the rail lock assembly 750 comprises a clamp rod 752, a clamp actuator 754 defining a clamp rod slot 756, and a spring 758 operatively connected to the clamp actuator 754 and the third rail mount 730. The third rail mount 730 defines a clamp rod channel 760 that is perpendicular to the third holding channel. Preferably, the clamp rod channel 760 is positioned below the third holding channel 733. The spring 758 creates a biasing force against the clamp actuator 754 to bias the clamp actuator 754 away from the third rail mount 730. The clamp rod 752 has a pivotable connection 762 to the fourth rail mount 740 and a slidable connection to the third rail mount 730 via the clamp rod channel 760. The clamp actuator 754 is movable between a first configuration and a second configuration. In the first configuration, a portion of the clamp actuator 754 is pushed away from the third rail mount 730 and the clamp rod slot 756 and the clamp rod channel 760 are slightly offset preventing the clamp rod 752 from sliding through the clamp rod slot 756 due to the friction against the clamp actuator 754. In the second configuration, the clamp actuator 754 is pressed flat against the third rail mount 730 and the clamp rod slot 756 and the clamp rod channel 760 are aligned allowing the clamp rod 752 to slide through both the clamp rod slot 756 and the clamp rod channel 760. The clamp actuator 754 can be placed in the second configuration by applying force to the clamp actuator 754 in a direction opposite the force of the spring 758.

Therefore, to adjust the main rail 408, the user simply presses the clamp actuator 754 towards the third rail mount 730 to align the clamp rod slot 756 of the clamp actuator 754 with the clamp rod channel 760 on the third rail mount 730. With the clamp rod channel 760 and the clamp rod slot 750 aligned, the third rail mount 730 is allowed to slide freely along the clamp rod 752 towards or away from the fourth rail mount 740. Although the third rail mount 730 moves in an arcuate path, due to the rotatability of the clamp rod 752 at the fourth rail mount 740, the arcuate path does not hinder the movement of the third rail mount 730 along the clamp rod 752. However, when the clamp actuator 754 is released, the clamp rod slot 756 and the clamp rod channel 760 are offset and the portion of the clamp actuator 754 defining the clamp rod slot 756 abuts against the clamp rod 752, thereby creating sufficient friction to prevent the third rail mount 730 from sliding along the clamp rod 752 thereby effectively locking the distal end 464 of the main rail 408 at a different position. Since the third rail mount 730 slides along the clamp rod 752, the user is able to move the distal end 464 of the main rail 408 in gradual, non-discrete increments.

Figure 7A:
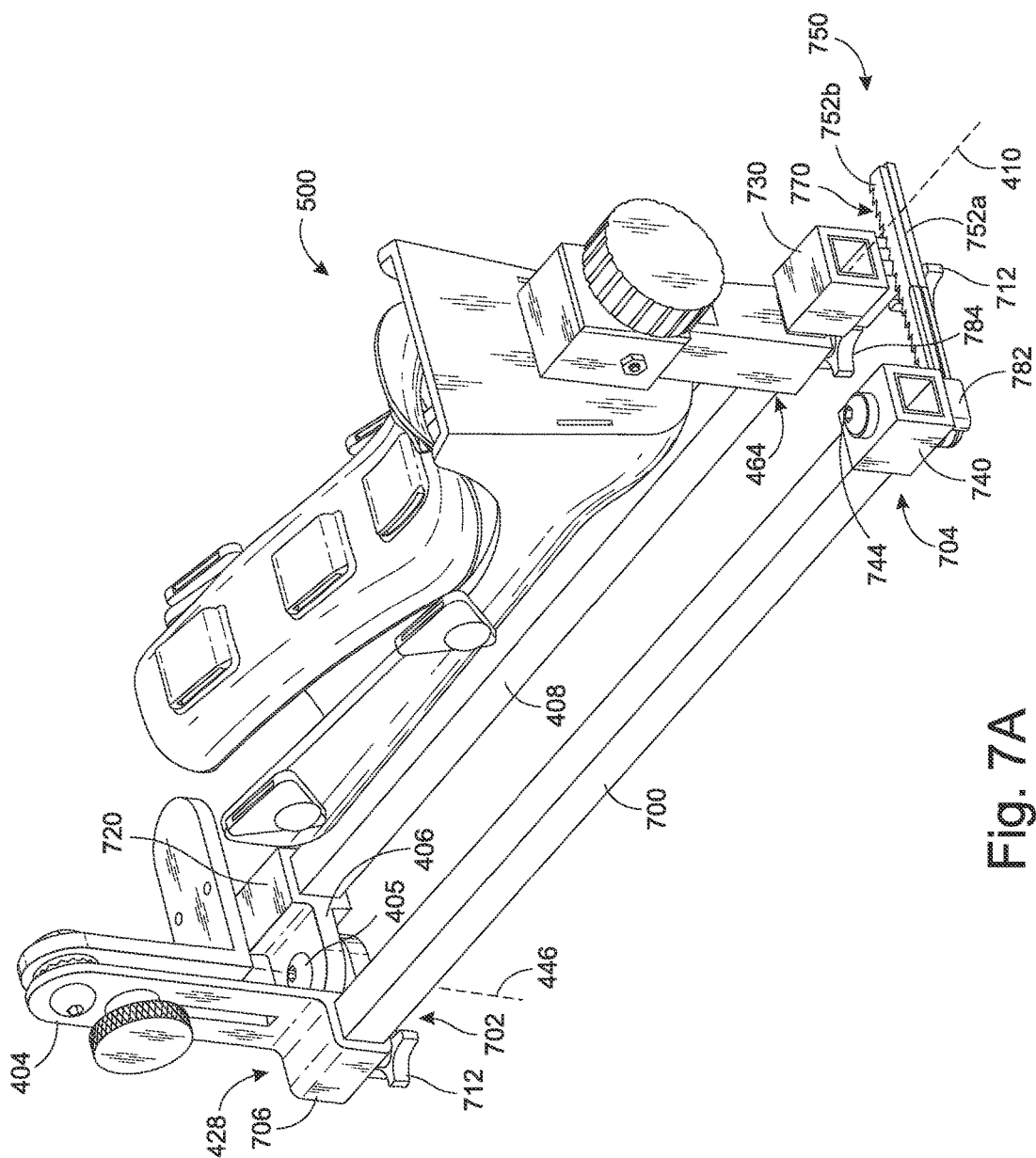
FIG. 7A is a perspective view of another embodiment of the present invention.
Figure 7B:
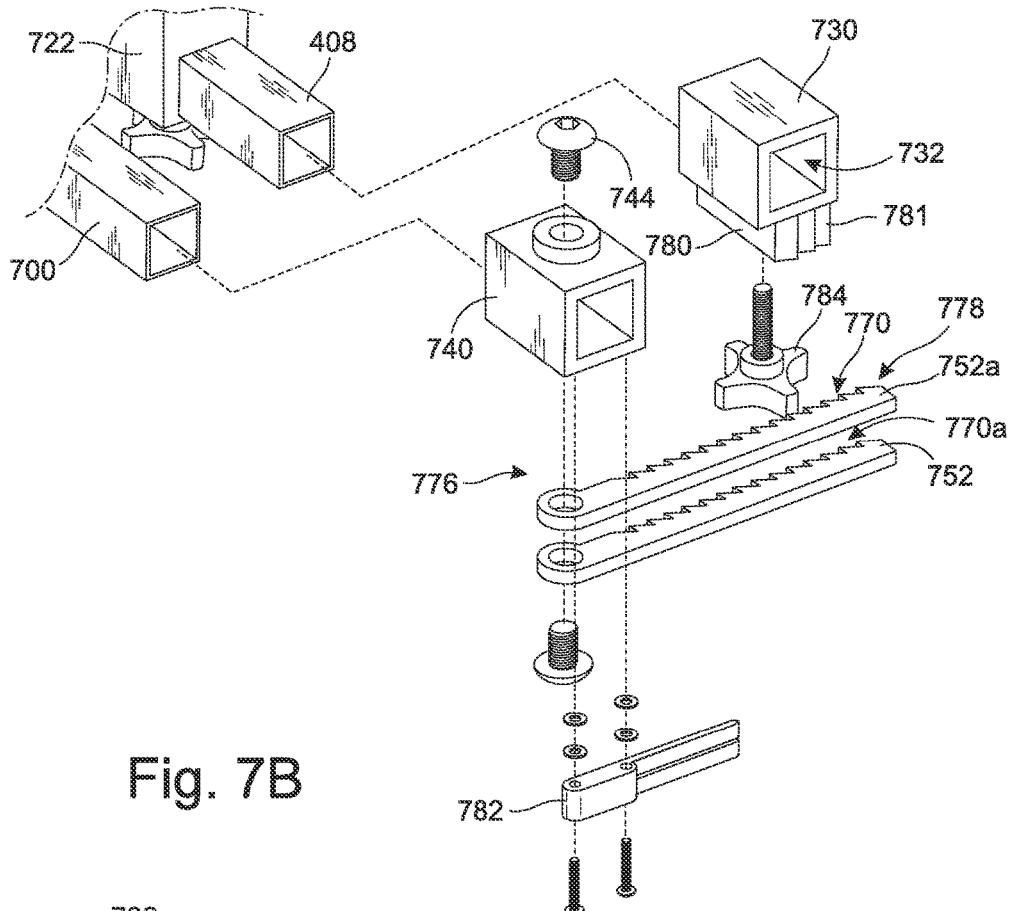
FIG. 7B is an exploded view of an embodiment of the rail lock assembly shown in FIG. 7A.
Figure 7C:
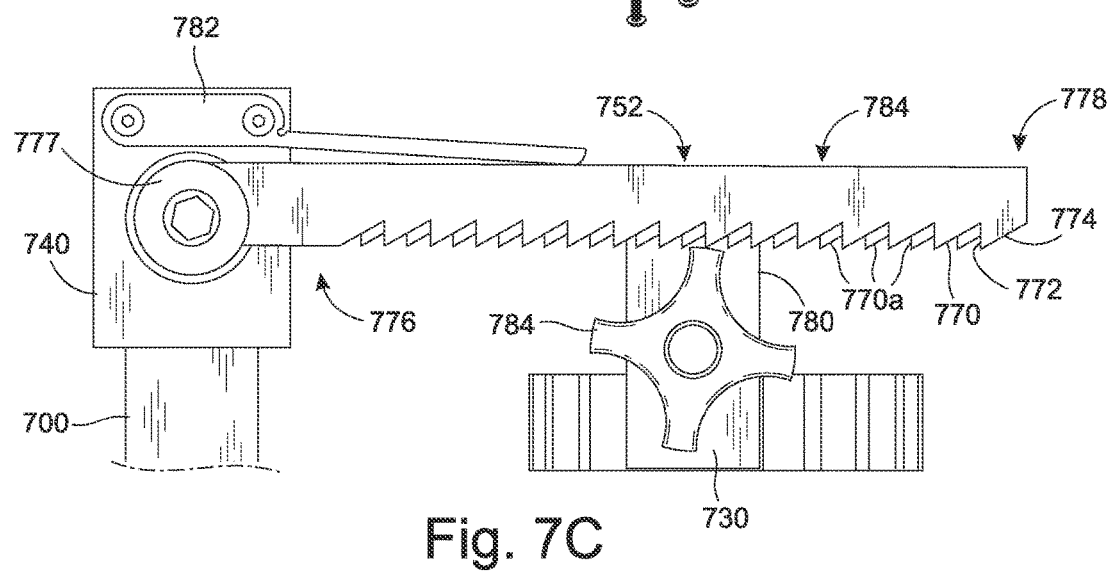
FIG. 7C is a bottoms view of the rail lock assembly shown in FIG. 7A.

In another embodiment, as shown in FIGS. 7A-7C, rather than sliding in and out of a clamp rod channel 760 on the third rail mount 730, the rail lock assembly 750 uses a ratchet system. In the ratchet system, the clamp rod 752 may have teeth 770 along one side of the clamp rod 752 to form a ratchet arm. The teeth 770 of the ratchet arm are asymmetrical having a steep-slope side 772 and a gentle-slop side 774. The steep-slope side 772 of each tooth 770 faces a first end 776 of the clamp bar 752 pivotably attached to the fourth rail mount 740 by a pivoting connector 777 and the gentle-slope side 774 of each tooth 770 faces a second side 778 adjacent to the third rail mount 730. The third rail mount 730 may have a toothed stopper 780 below the third holding channel 733 that can engage with the teeth 770 of the clamp base 752. The third rail mount 730 may comprise a lock 784 to lock the third rail mount 330 against the main rail 408 at various positions. A spring 782, such as a leaf spring, on the smooth side 784 (opposite the teeth side), may bias the ratchet arm against the toothed stopper 780. The first end 776 of the clamp bar 752 is rotatably attached to the fourth rail mount 740 to allow the clamp bar 752 to pivot away from and back towards the third rail mount 730.

In use, the user can push the main rail 408 towards the fixed rail 700. The teeth 781 on the toothed stopper 780 slide along the gentle-slope side 774 pushing the clamp bar 752 away from the toothed stopper 780. Once the teeth 781 of the toothed stopper 780 pass the apex of the teeth 770 of the clamp bar 752, the spring 782 snaps the clamp bar 752 back towards the toother stopper 780 as the teeth 781 of the toothed stopper 780 fall in between the teeth 770 of the clamp bar. Due to the configuration of the steep-slope side 772, the main rail 408 is unable to move back to its original position. Using this method, the main rail 408 moves towards the fixed rail 700 in discrete movements.

To increase the level of discreteness, more teeth 770 can be added to the clamp bar 752. In some embodiments, to add more discreteness, a second clamp bar 752a may be supplied. For example, a second clamp bar 752a, identical to the first clamp bar 752 may be rotatably attached to the fourth rail mount 740 immediately above or below the first clamp bar 752 so as to be stacked, one on top of the other. The second clamp bar 752a, however, may be laterally offset from the first clamp bar 752 so that the teeth 770 of the first clamp bar 752 are not aligned with the teeth 770a of the second clamp bar 752a. Rather, the teeth 770a of the second clamp bar 752a are aligned with the gaps in between the teeth 770 of the first clamp bar 752. This configuration effectively doubles the discreteness of the single clamp bar 752 embodiment.

Figure 8:
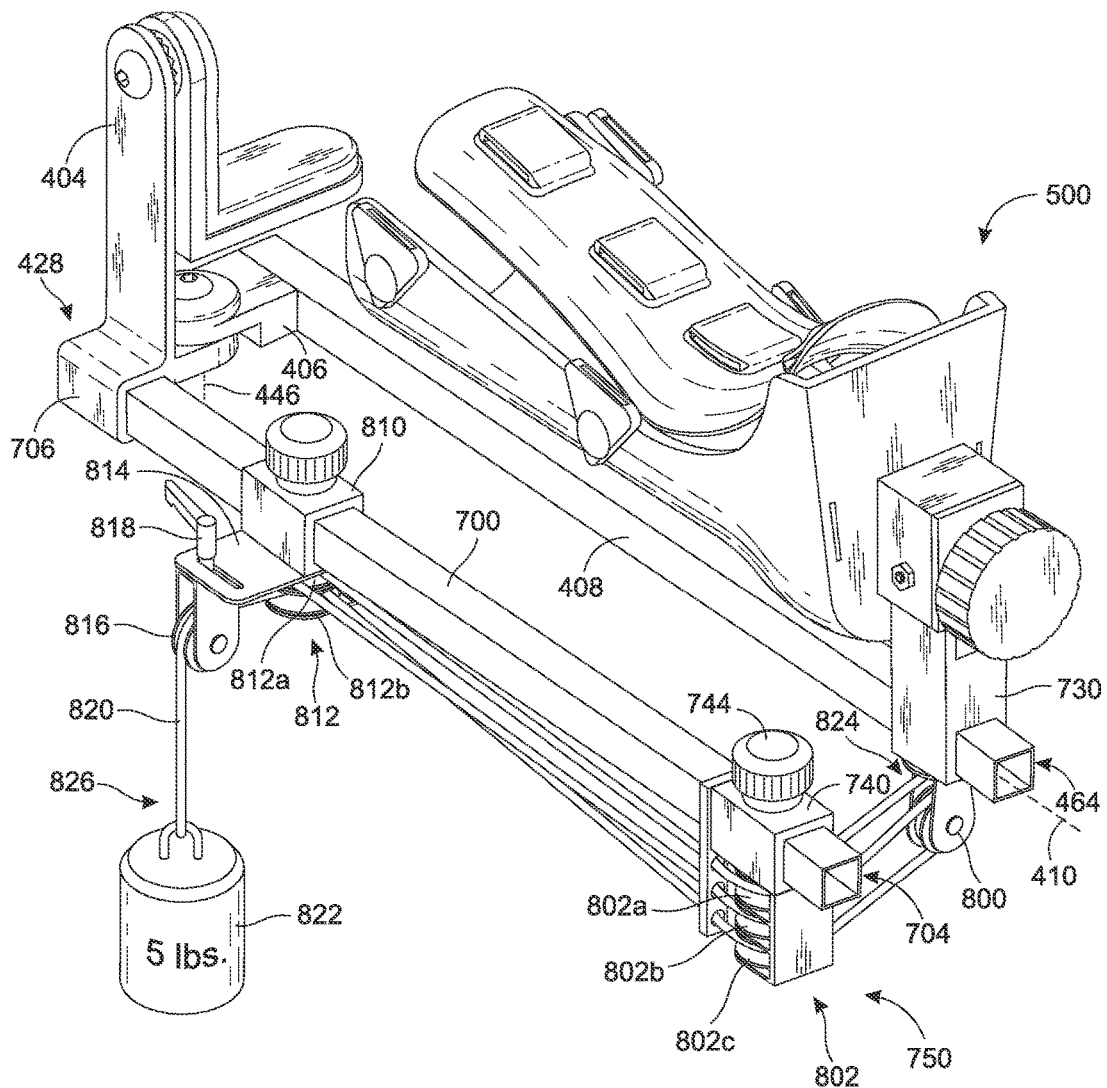
FIG. 8 is a perspective view of another embodiment of the present invention.

In another embodiment, as shown in FIG. 8, the rail lock assembly 750 utilizes a pulley system, rather than the clamp bar assembly, to impart a constant force on the patient's leg. The third rail mount 730 may comprises a vertically-arranged pulley 800 rather than the clamp rod 752 and clamp rod channel 760. The vertically-arranged pulley 800 may hang vertically from the bottom of the third rail mount 730. The fourth rail mount 740 may comprise a first set of horizontally-arranged pulleys 802. In the preferred embodiment, the first set of horizontally-arranged pulleys 802 comprises a plurality of pulleys 802a-c, one stacked on top of the other with their centers of rotations coaxially aligned.

A fifth rail mount 810 is mounted on the fixed rail 700 in between the first rail mount 706 and the fourth rail mount 740. The fifth rail mount 810 comprises a second set of horizontally-arranged pulleys 812 comprising a plurality of pulleys 812a, 812b, one stacked on top of the other with their centers of rotation coaxially aligned. Projecting away from the fifth rail mount 810 is a pulley bracket 814 comprising a second vertically-arranged pulley 816 adjacent to the second set of horizontally-arranged pulleys 812. An adjuster 818 may be provided to allow the second vertically-arranged pulley 816 to be adjusted relative to the second set of horizontally-arranged pulleys 812. A cable 820 is looped through the pulley system to provide a system that allows a weight 822 attached to the pulley system to impart a constant force on the main rail 408 at the distal end 464 towards the distal end 704 of the fixed rail 700.

For example, the first set of horizontally-arranged pulleys 802 may have 3 pulleys stacked on top of each other, a top pulley 802a, an intermediate pulley 802b, and a bottom pulley 802c. The second set of horizontally-arranged pulleys 812 may have 2 pulleys stacked on top of the other, a top pulley 812a and a bottom pulley 812b. The first end 824 of the cable 820 may be fastened to the third rail mount 730, for example, to a rod directly above the first vertically-arranged pulley 800. The second end 826 of the cable 820 can then be fed through the top pulley 802a in the first set of horizontally-arranged pulleys 802, then change directions to head towards the top pulley 812a in the second set of horizontally-arranged pulleys 812, then reversed directions back towards the intermediate pulley 802*b* of the first set of horizontally-arranged pulleys 802, then change directions to head towards the first vertical pulley 800 on the third rail mount 730, then reverse directions and feed through the bottom pulley 802*c* of the first set of horizontally-arranged pulleys 802, then change directions towards the bottom pulley 812*b* of the second set of horizontally-arranged pulleys 812, then change directions towards the second vertical pulley 816 and descend to attach to a weight 822, like a block and tackle system. The advantage of the system is that as the patient's thigh and leg settles throughout surgery, the surgeon does not need to adjust any clamping or locking mechanisms to maintain the space in the knee joint because the constant force of the hanging weight will adjust the patient's leg by keeping a constant force on the patient.

Figure 1E:
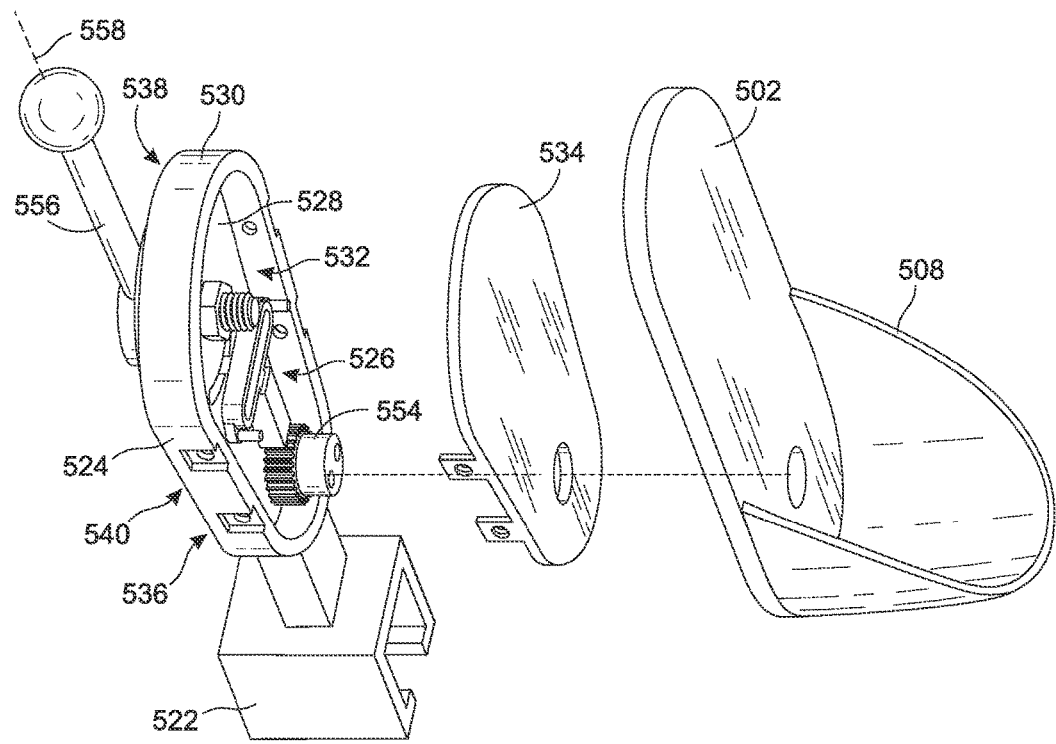
FIG. 1E is a partially exploded view of the foot brace.
Figure 1F:
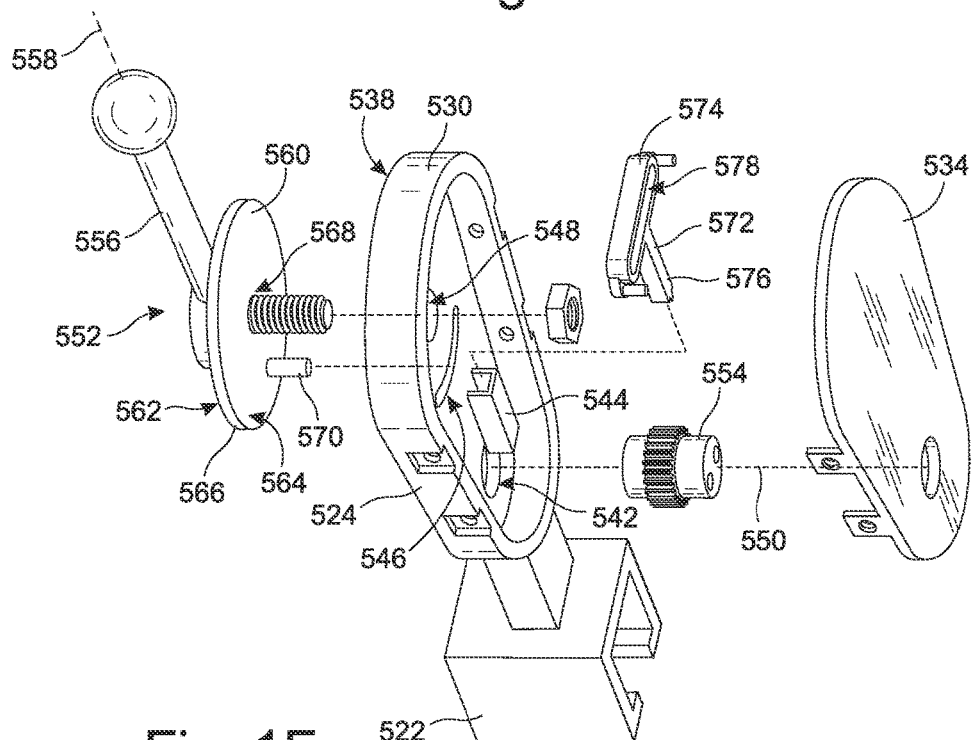
FIG. 1F is an exploded view of the rotation lock assembly of the foot brace.
Figure 5A:
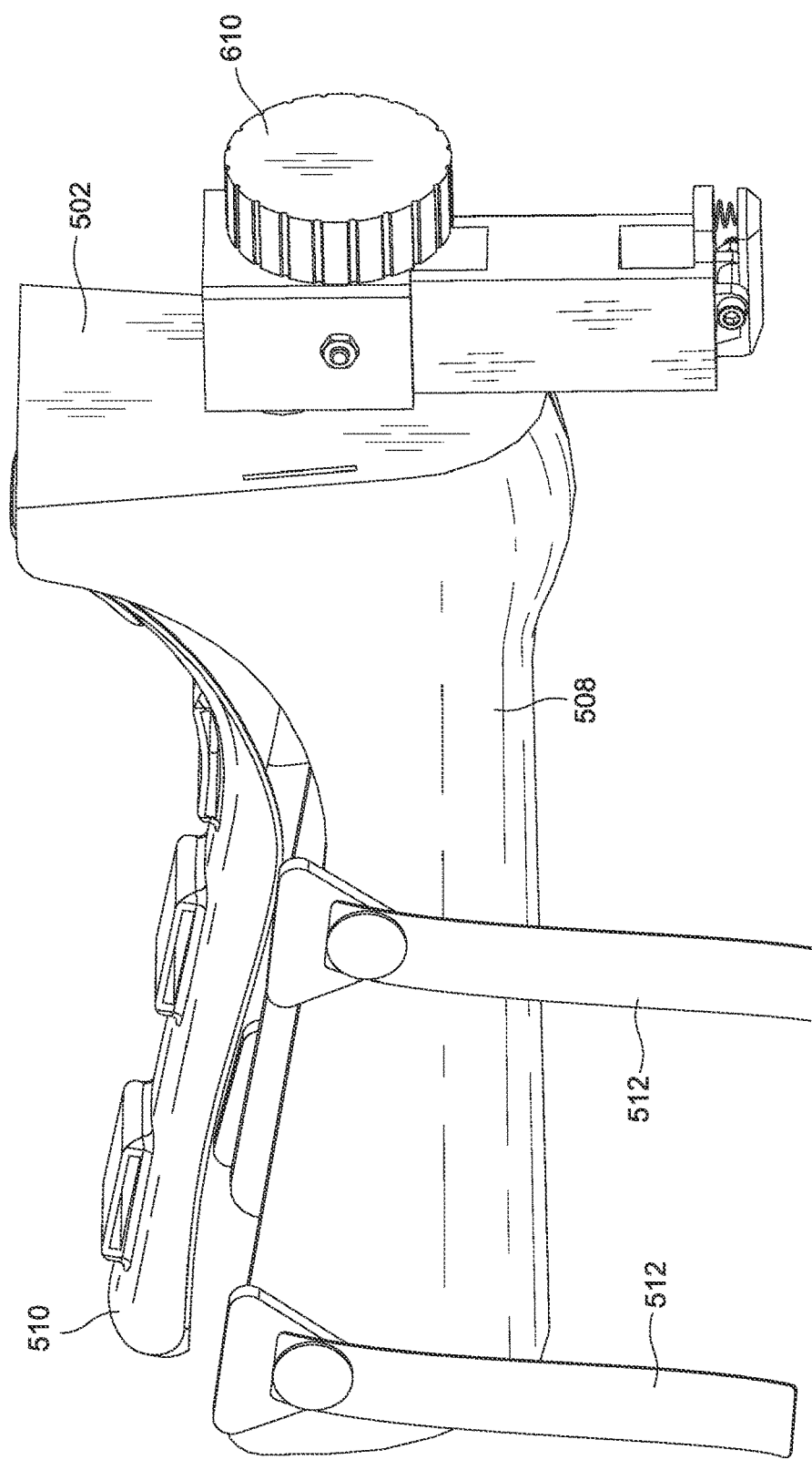
FIG. 5A is a perspective view of an embodiment of the foot brace.

To facilitate support for the lower leg, a foot brace 500 is attached to the distal end 464 of the main axle 408. As shown in FIGS. 1E and 1F, in the preferred embodiment, the foot brace 500 comprises a plantar portion 502 having a heel end 504 and a toe end 506 opposite the heel end 504, and a heel portion 508 extending substantially perpendicularly from the plantar portion 502 at the heel end 504. This allows the heel of the patient to be placed on the heel portion 508 with the bottom of the patient's foot placed against the plantar portion 502 of the foot brace. In some embodiments, the foot brace 500 may further comprise a shin portion 510, as shown in FIG. 5. This allows most of the lower leg to be covered by the foot brace 500 like a boot. In the preferred embodiment, the shin portion 510 may be a hard conforming shell. The hard conforming shell on top will discourage the unwanted distraction in the ligaments of the ankle during the surgical procedure. This will also minimize the foot from moving or rotating inside the boot. Bindings 512 may be used to compress the shin portion 510 and the heel portion 508 together to secure the lower leg in place. For example, bindings 512 may include, straps, elastic wraps, ties, clips and the like. The bindings 512 may be secured by hook-and-loop fasteners, snap buttons, ties, hooks, locks, and the like.

Figure 4A:
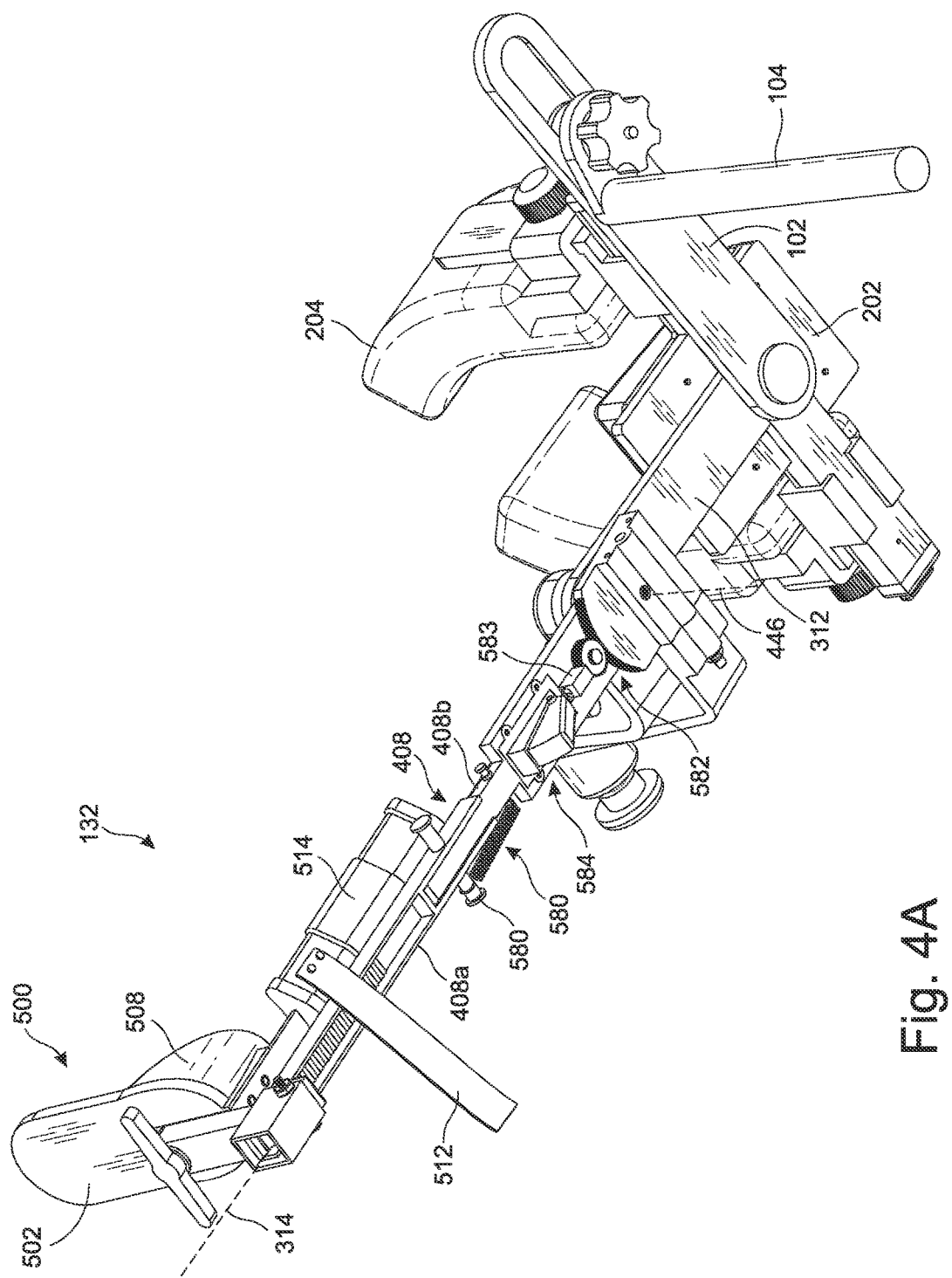
FIG. 4A is a perspective view from the bottom of another embodiment of the present invention.

Other configurations of the foot brace 500 may be used. For example, bindings 512 may be provided to secure the foot in place against the heel portion 508 with or without this shin portion 510 as shown in FIGS. 3 and 4. In embodiments with a binding 512, the heel portion 508 may extend further up along the calves of the patient, as shown in FIGS. 3 and 5. Alternatively, a separate binding holder may be utilized to allow the patient's leg to be secured by bindings. Therefore, in some embodiments, the foot brace 500 may be in the form of a boot. In some embodiments, a calf portion 514 may be provided separate from the heel portion 508 as shown in FIG. 4A. Again bindings 512 may be provided to strap the shin against the calf portion 514. Although different embodiments of the foot brace 500 (with heel portion 508, without heel portion 508, with calf portion 514, without calf portion 514, and any combination thereof) have been shown with different embodiments of the surgical leg positioner 10, any foot brace 500 can be used with any embodiment of the surgical leg positioner 10.

In order to allow for adjustments of the leg, the foot brace 500 may comprise a rotation lock base 520. The rotation lock base 520 is configured to move along the length of the main axle 408 to accommodate legs of different lengths, and to rotate the foot in a clockwise or counterclockwise manner about an axis perpendicular to the plantar portion 502 and parallel to the main axle 408. In the preferred embodiment, the rotation lock base 520 comprises a clamp portion 522 slidably mounted on the main axle 408, a rotation lock housing 524 connected to the clamp 522, and a rotation lock assembly 526.

The clamp portion 522 mounts on the main axle 408 in a manner that allows the clamp 522 to slide along the length of the main axle 408. The clamp 522 may have a lock to fix the clamp at a desired location along the main axle 408, such as an adjustable clamp, pins, gears, and the like. In the preferred embodiment, the main axle 408 has a non-cylindrical exterior surface and the clamp 522 has a non-cylindrical interior surface to mate with the main axle 408 in a manner that prevents rotation of the clamp 522 about the main axle 408. For example, the clamp 522 may be in the form of a C-clamp.

In the preferred embodiment, the rotation lock housing 524 comprises a floor plate 528 and an elevated wall 530 surrounding the floor plate 528 to define a cavity 532 to hold the components of the rotation lock assembly 526. A cover 534 may be provided to enclose the rotation lock assembly 526 inside the cavity 532. The floor plate 528 comprises a heel end 536 and a toe end 538 opposite the heel end 536 with a middle section 540 therebetween. At the heel end 536 of the floor plate 528 is a first opening 542. Preferably, the first opening 542 is circular in shape. Above the first opening 542 in the direction of the toe end 538 is a slide bracket 544 defining a channel. Above the slide bracket 544 towards the toe end 538 is an arcuate slot 546 with the ends of the arcuate slot 546 pointed towards the toe end 538. At a point defining the center point of the circle that defines the arcuate slot 546 is a second opening 548.

The rotation lock assembly 526 is configured to allow the foot brace 500 to rotate in a clockwise or counterclockwise direction about a heel axis 550 defined by the center of the first hole 542 of the floor plate 528. Therefore, the foot is able to rotate in a clockwise or counterclockwise direction about the heel axis 550 located approximately at the heel of the patient's foot, thereby allowing the toes to move along an arcuate path.

In the preferred embodiment, the rotation lock assembly 520 comprises an adjustable handle 552, a spur gear 554 rotatable within the rotation lock housing 524, and a spur gear pin 572 slidably mounted to the rotation lock housing 524 in the slide bracket 544 in between the adjustable handle 552 and the spur gear 554. The adjustable handle 552 comprises a handle portion 556 defining a longitudinal handle axis 558, and a disc portion 560 comprising an exterior surface 562, an interior surface 564 opposite the exterior surface 562, a perimeter 566 defining the bounds of the interior and exterior surfaces 562, 564, and a center 568. The handle portion 556 may be attached to the disc portion 560, preferably at the center 568 of the disc portion 560 with the handle portion 556 projecting out past the perimeter 566 of the disc portion 560. A guide pin 570 may be protruding from the interior surface 564 of the disc 560 adjacent to the perimeter 566 and in line with the longitudinal handle axis 558. The center 568 of the disc portion 560 may be rotatably mounted to the rotation lock housing 524 at the second opening 548 with the guide pin 570 protruding through the arcuate slot 546.

The spur gear 554 is attached to the floor plate 528 through the first hole 542 and provides the mechanism for rotation of the foot brace 500 and the ability to lock the foot brace 500 in any orientation. Therefore, the spur gear 554 may be connected to the floor plate 528 adjacent to the heel end 536. In the preferred embodiment, the spur gear 554 comprises a toothed perimeter and is rotatable about the longitudinal heel axis 550.

In the preferred embodiment, the spur gear pin 557 comprises a handle engagement portion 574 and a spur gear engagement portion 576. The handle engagement portion 574 and spur gear engagement portion 576 may be arranged in a T-configuration with the handle engagement portion 576 comprising a horizontal slot 578 into which the guide pin 570 resides, and the spur gear engagement portion 576 is configured to slide up and down within the slide bracket 544 to engage the toothed perimeter of the spur gear 554. Due to the arcuate shape of the arcuate slot 546, rotation of the adjustable handle 556 in either the clockwise or counter-clockwise direction causes the guide pin 570 to slide within the slot 546 to move the spur gear engagement portion 576 in an upward direction to disengage from the spur gear 554. Returning the adjustable handle back to its neutral position lowers the spur gear engagement portion 576 and engages the spur gear 554 to lock the foot brace in place. Due to the bidirectional rotation of the adjustable handle, the surgeon can push the handle 556 in the direction of the foot rotation.

In some embodiments, a gear mechanism 612 attached to a knob 610 may be used so that rotation of the knob 610 causes rotation of the gears 612 which in turn causes rotation of the foot brace 500, as shown in FIG. 5. In the preferred embodiment, the gear mechanism 612 comprises a worm gear. In some embodiments, the foot brace 500 may be mounted on a cylindrical pin and secured with a locking mechanism. The locking mechanism allows the foot brace 500 to rotate about the cylindrical pin. Locking the locking mechanism secures the foot brace 500 in position.

Figure 1H:
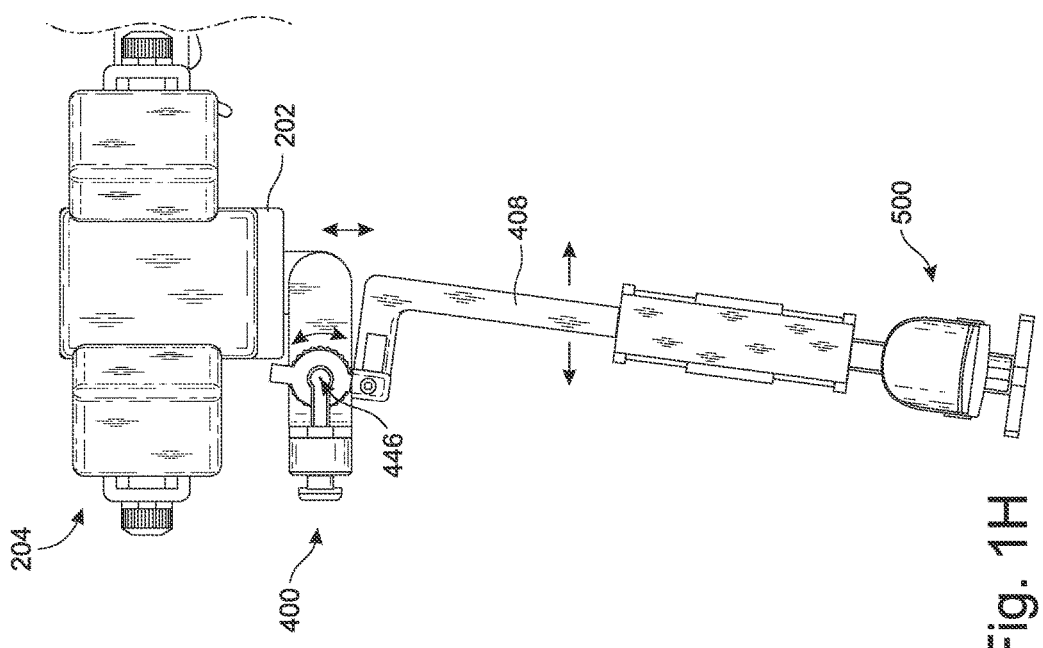
FIG. 1G-1H is a top plan view of an embodiment of the present invention showing the leg positioner in the neutral position (FIG. 1G) and in valgus (1H) for the right leg.
Figure 1G:
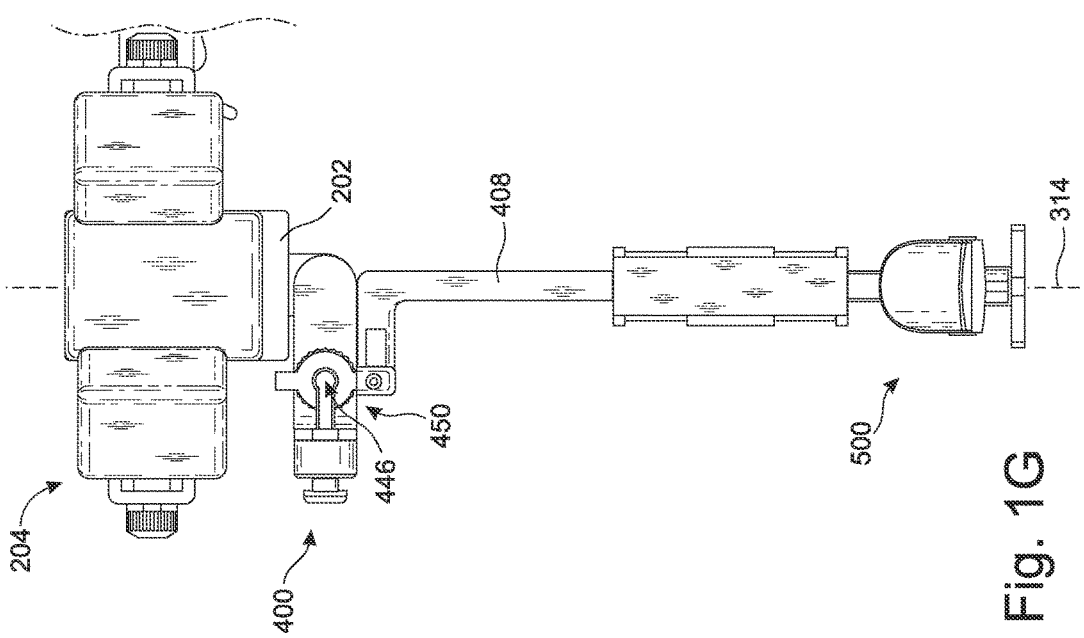

As shown in FIGS. 1G and 1H, in the preferred embodiment, the base frame 202, the main axle 408, and the foot brace 500 are linearly aligned along the main axis 314 and the lateral end 450 of the horizontal bracket 406, and thus the second joint axis 446, is laterally offset from the main axis 314. This configuration allows for the simultaneous longitudinal distraction and varus/valgus movement at the knee (as shown by arrows in FIG. 1H) when the main axle 408 is rotated about the second joint axis 446. With this configuration, simultaneous longitudinal distraction and varus/valgus movement at the knee can be accomplished without the need of any kind of barrier used to block the knee in order to achieve the varus/valgus movement.

Figure 4B:
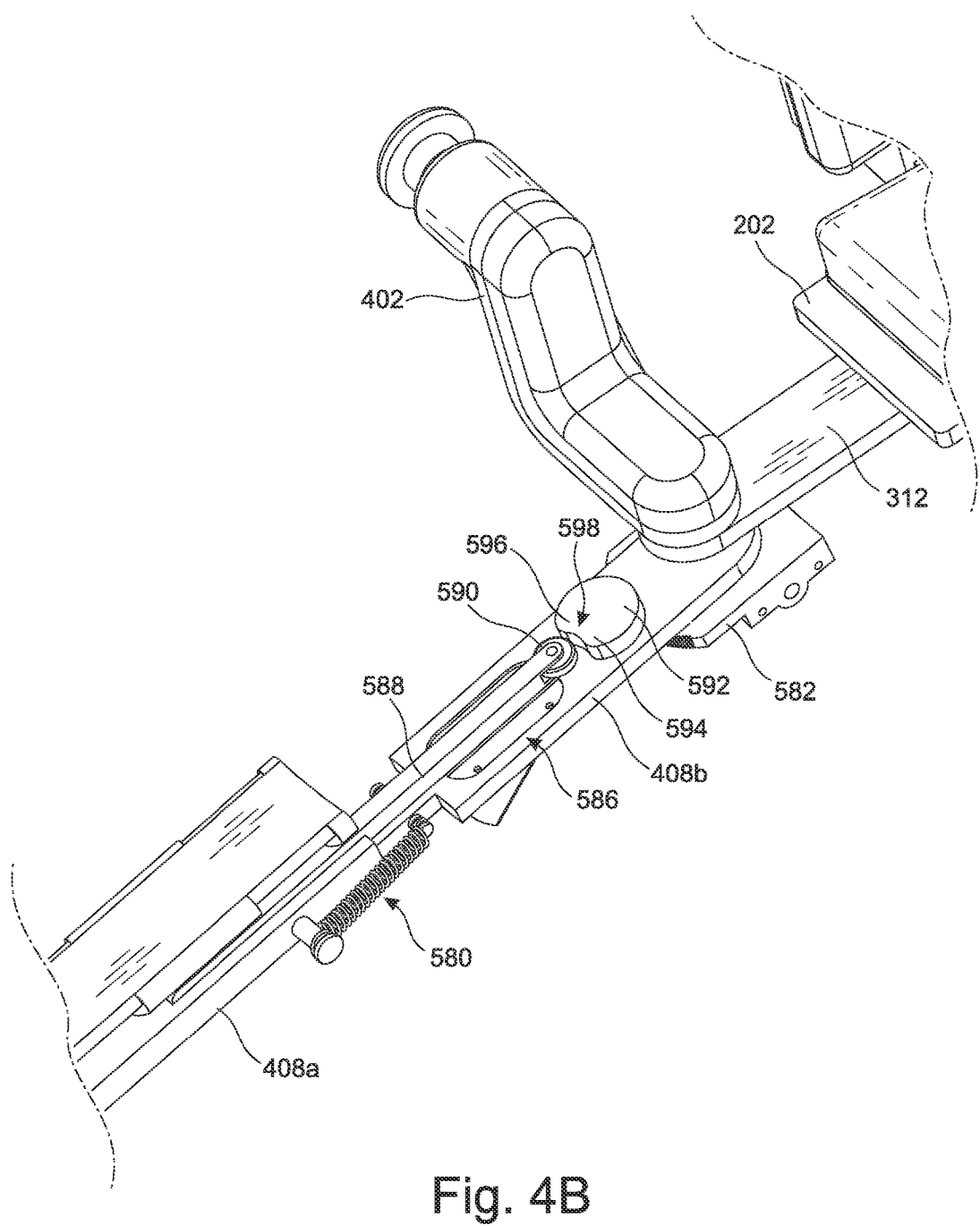
FIG. 4B is a close up perspective view of a two piece main axle embodiment of the present invention.
Figure 4C:
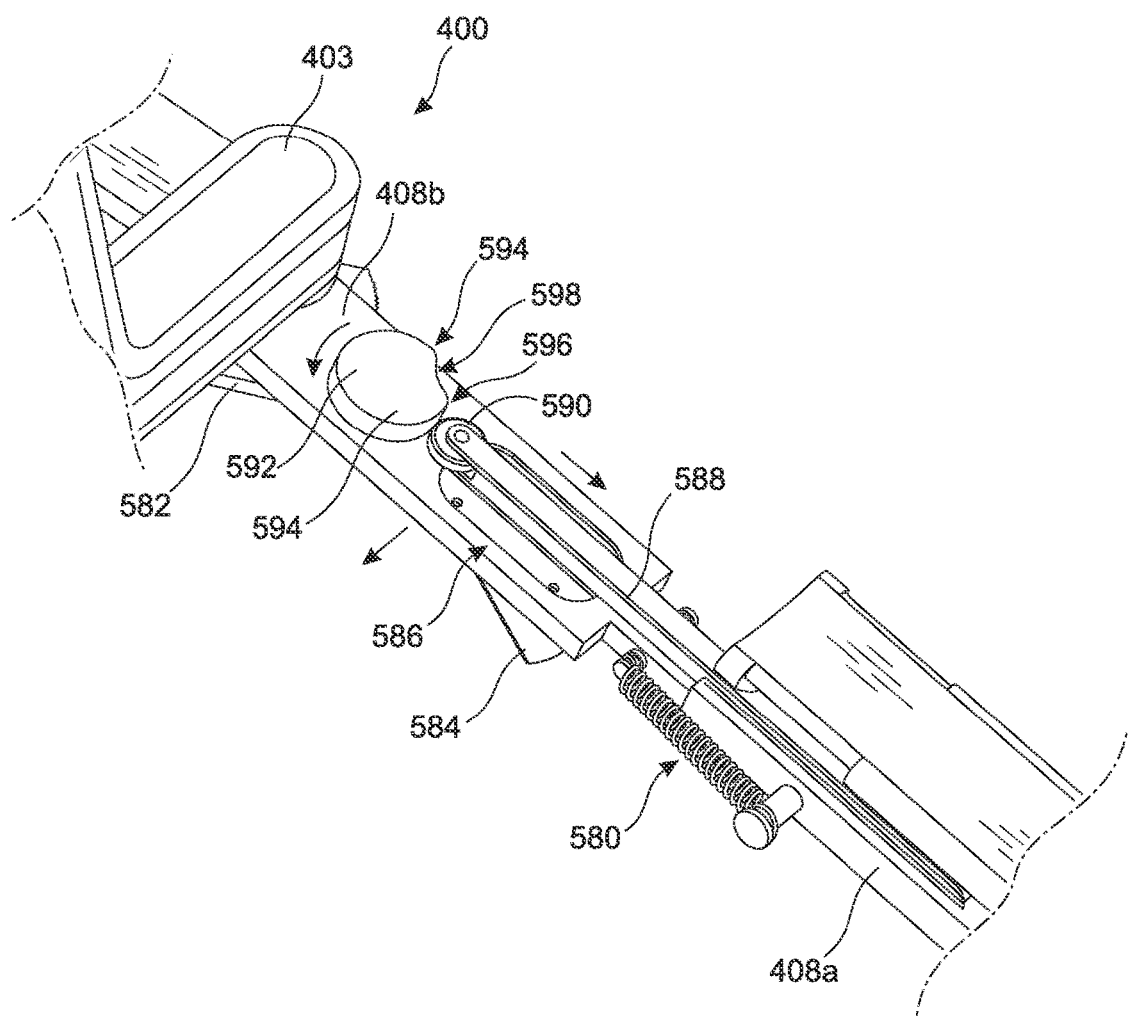
FIG. 4C is the embodiment shown in FIG. 4B in a position to place the right leg in valgus.

In another embodiment, in order to allow for longitudinal distraction as well as varus/valgus movement, rather than having the second joint axis 446 offset from the main axis 314, the second joint axis 446 may be in line with the main axis 314, as shown in FIGS. 4A-4C. In such an embodiment, the main axle 408 may be a two-piece axle (distal axle 408a and proximal axle 408b) permitting telescoping action so as to elongate or shorten the length of the main axle 408. A tensioning mechanism 580 may be provided to lock the desired length of the main axle 408. A gear mechanism 582 may be utilized at the second joint 446 to allow the main axle 408 to move in the varus/valgus direction. A trigger lock 584 may be utilized to lock the main axle 408 in place or unlock the main axle 408 for varus/valgus movement by engaging or disengaging a pin 583 from the gear mechanism 582. Extending from the distal axle 408a towards the proximal axle 408b is a wheeled shaft 586 having a shaft portion 588 and a wheeled portion 590 located at the end of the shaft portion opposite the distal axle 408a. On the proximal axle 408b is a cam 592 that, when rotated, causes the distal axle 408a to be distracted from the proximal axle 408b. In the preferred embodiment, the cam 592 comprises two lobes 594, 596 and a divot therebetween 598 in a heart-shaped configuration. The cam 592 is operatively connected to the gear mechanism 582 such that when the gears 582 rotate in one direction, the cam 592 rotates in the opposite direction. In a neutral position, the wheeled portion 590 resides in the divot 598 as shown in FIG. 4B.

Therefore, a patient's upper leg may be secured in the thigh brace 204. The lower leg may be secured to the foot brace 500. The tensioning mechanism 580 may be a spring imparting a biasing force on the distal axle 408a to move towards the proximal axle 408b. Once the leg is positioned on the leg positioner 10, the lower leg is pushed towards the upper leg due to the tensioning mechanism 580. When the leg is moved in varus or valgus, the main axle 408 moves the leg laterally about the second joint axis 446. Simultaneously, the cam 592 rotates in the opposite direction. This causes the wheeled portion 590 to move from the divot 598 to one of the lobes 594, 596. When the wheeled portion 590 rides along one of the lobes 594, 596, then the shaft portion 588 is pushed distally away from the proximal axle 408b. Since the shaft portion 588 is attached to the distal axle 408a, the distal axle 408a moves distally away from the proximal axle 408b. Since the lower leg is attached to the distal axle 408a via the foot brace 500, the lower leg is distracted from the upper leg while simultaneously undergoing varus or valgus.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A surgical leg positioner, comprising:
   a. a surgical bed clamp, comprising:
      i. a base clamp,
      ii. a vertical post protruding from the base clamp,
      iii. a compression plate attached to the vertical post, wherein the compression plate comprises a first plate portion, a second plate portion, a narrow gap defined therebetween to allow the first plate portion and the second plate portion to be compressed, a compression lock inserted through the compression plate and configured to compress and release the first and second plate portions against each other, and a horizontal channel, and
      iv. a horizontal post perpendicular to the vertical post and protruding from the horizontal channel of the compression plate, the horizontal post having a first end, and a second end opposite the first end, wherein the compression plate is mounted adjacent to the first end of the horizontal post and configured to slide along the horizontal post and be clamped along the horizontal post;
   b. a thigh clamp module mounted on the surgical bed clamp and operatively attached to the second end of the horizontal post, the thigh clamp module comprising:
      i. a base frame comprising a proximal end, a distal end opposite the proximal end, a pair of opposing side ends adjacent to the distal end and the proximal end, a first lateral extension and a second lateral extension projecting laterally away from each other from their respective opposing side ends, each of the first and second lateral extensions terminating at a lateral free end, wherein the proximal end, distal end, opposing side ends, and first and second lateral extensions define a top surface and a bottom surface opposite the top surface, wherein the top surface comprises a lateral channel extending substantially from the lateral free end of the first lateral extension to the lateral free end of the second lateral extension, and a distal extension projecting from the distal end and away from the proximal end of the base frame, ii. a rack and pinion assembly comprising a pinion centrally located in the lateral channel, a first rack operatively connected to the pinion on one side of the pinion, a second rack operatively connected to the pinion on the diametrically opposite side of the pinion, iii. a brace lock assembly configured to lock the rack and pinion assembly at a desired location, the brace lock assembly comprising a ratchet mounted on the opinion, a pawl operatively connected to the ratchet to permit rotation of the ratchet in one direction, a trigger connected to the pawl, the trigger having a first end and a second end opposite the first end and a mounting pin therebetween, a first trigger rod attached to the first end of the trigger and extending perpendicularly away from the trigger in a first direction, a second trigger rod attached to the second end of the trigger and extending perpendicularly away from the trigger in a second direction opposite of the first direction, a first trigger button attached to the first trigger rod, a second trigger button attached to the second trigger rod, wherein depression of the first trigger button or the second trigger button causes the trigger to rotate about the mounting pin and disengage from the ratchet allowing the first and second racks to slide along the lateral channel, a first spring operatively connected to the first trigger rod and a second spring operatively connected to the second trigger rod, the first and second springs imparting a laterally biasing force against the first and second trigger rods, respectively, causing the pawl to engage the ratchet, iv. a flat base frame cap comprising a proximal end, a distal end opposite the proximal end, a pair of opposing side ends adjacent to the distal end and the proximal end, and a pair of guide arms projecting laterally away from each other from their respective side ends, each guide arm comprising a guide arm slot, and v. a thigh brace connected to the first and second racks, the thigh brace comprising a pair of side pads, each side pad mounted on its own side pad frame, each side pad frame movably mounted on a pad frame bracket, wherein each side pad frame is defined by an interior face and an exterior face, the exterior face comprising an exterior slot and a tightening bolt, each pad frame bracket comprising a sliding bracket and a support arm, wherein the exterior slot is configured to slide along the support arm and the tightening bolt is configured to tighten each side pad frame at any point along its respective support arm, wherein each sliding bracket is connected to its respective rack through their respective guide arm slots on their respective guide arms, and a base pad mounted on the base frame cap;

c. a swing arm module attached to the distal extension, the swing arm module comprising:

i. a base arm having an L-shape configuration comprising a vertical arm and a horizontal arm, wherein the vertical arm has a first terminal end, the horizontal arm has a second terminal end, and wherein the second terminal end is connected to the distal extension, ii. a vertical bracket comprising an upper end and a lower end opposite the upper end, the upper end attached to the vertical arm of the base arm at a toothed-gear and configured to rotate about a first joint axis defined by the toothed gear, the vertical bracket comprising a brake slot through which the toothed-gear protrudes, and a slide brake slidably mounted within the brake slot, the slide brake having a first end, a second end opposite the first end, and a handle therebetween, the first end of the slide brake comprising a toothed-end configured to engage the toothed-gear, a third spring positioned in the brake slot abutting the second end of the slide brake to impart a biasing force against the second end of the slide brake causing the toothed-end to engage the toothed-gear, the lower end comprising a first rail mount defining a first holding channel, iii. a horizontal bracket having a medial end and a lateral end, the lateral end rotatably connected to the lower end of the vertical bracket, the medial end comprising a second rail mount defining a second holding channel, iv. a main rail having a proximal end, a distal end opposite the proximal end, a first side adjacent to the proximal end and the distal end, and a second side opposite the first side and adjacent to the proximal end and the distal end, wherein the horizontal bracket is operatively connected to the proximal end of the main rail via the second rail mount, and the distal end of the main rail attached to a third rail mount defining a third holding channel and a clamp rod channel perpendicular to the third holding channel, v. a fixed rail adjacent and lateral to the main rail, the fixed rail comprising a proximal end and a distal end, wherein the proximal end of the fixed rail is operatively connected to the first rail mount, and the distal end of the fixed rail is adjacent to the third rail mount and operatively connected to a fourth rail mount defining a fourth holding channel, and vi. a rail lock assembly, comprising a clamp rod, a clamp actuator defining a clamp rod slot, and a spring operatively connected to the clamp actuator and the third rail mount, the spring creating a biasing force against the clamp actuator to bias the clamp actuator away from the third rail mount, wherein the clamp rod is rotatably connected to the fourth rail mount and slidably connected to the third rail mount via the clamp rod channel, wherein the clamp actuator is movable between a first configuration and a second configuration, wherein in the first configuration, the clamp rod slot and the clamp rod channel are slightly offset preventing the clamp rod to slide through the clamp rod slot, and in the second configuration, the clamp rod slot and the clamp rod channel are aligned allowing the clamp rod to slide through both the clamp rod slot and the clamp rod channel;

d. a foot brace, comprising a plantar portion having a heel end and a toe end opposite the heel end, and a heel portion extending substantially perpendicularly from the plantar portion at the heel end; and e. a rotation lock base operatively connected to the foot brace, the rotation lock base comprising an adjustable handle, and a plurality of gears, wherein the adjustable handle rotates the plurality of gears to rotate the foot brace.

2. A surgical leg positioner, comprising:
a. a surgical bed clamp;
b. a thigh clamp module mounted on the surgical bed clamp; and
c. a swing arm module attached to the thigh clamp module, the swing arm module comprising a vertical bracket, a main rail operatively connected to the vertical bracket, and a fixed rail adjacent to the main rail, the fixed rail operatively connected to the vertical bracket, wherein the main rail comprises a first proximal end and a first distal end and defines a main rail axis, wherein the fixed rail comprises a second proximal end and a second distal end opposite the second proximal end, wherein the second distal end is adjacent to the first distal end of the main rail, wherein the first proximal end of the main rail is rotatably attached at a joint to the vertical bracket to allow the first distal end of the main rail to move in an arcuate path towards the second distal end of the fixed rail
d. wherein the thigh clamp module comprises:
  i. a base frame comprising a proximal end, a distal end opposite the proximal end, a pair of opposing side ends adjacent to the distal end and the proximal end, a first lateral extension and a second lateral extension projecting laterally away from each other from their respective opposing side ends, each of the first and second lateral extensions terminating at a lateral free end, wherein the proximal end, distal end, opposing side ends, and the first and second lateral extensions define a top surface and a bottom surface opposite the top surface, wherein the top surface comprises a lateral channel extending substantially from the lateral free end of the first lateral extension to the lateral free end of the second lateral extension, and a distal extension projecting from the distal end and away from the proximal end of the base frame;
  ii. a rack and pinion assembly comprising a pinion centrally located in the lateral channel;
  iii. a brace lock assembly configured to lock the rack and pinion assembly at a desired location; and
  iv. a thigh brace connected to the rack and pinion assembly, the thigh brace comprising a pair of side pads, wherein the rack and pinion assembly allows the pair of side pads to move towards and away from each other, wherein the rack and pinion assembly comprises a first rack operatively connected to the pinion on one side of the pinion; a second rack operatively connected to the pinion on the diametrically opposite side of the pinion, wherein each side pad is attached to one of the racks,
  v. wherein the brace lock assembly comprises a ratchet mounted on the pinion, a pawl operatively connected to the ratchet to permit rotation of the ratchet in one direction, a trigger connected to the pawl, the trigger having a first end and a second end opposite the first end and a mounting pin therebetween, a first trigger rod attached to the first end of the trigger and extending perpendicularly away from the trigger in a first direction, a second trigger rod attached to the second end of the trigger and extending perpendicularly away from the trigger in a second direction opposite of the first direction, a first trigger button attached to the first trigger rod, a second trigger button attached to the second trigger rod, wherein depression of the first trigger button or the second trigger button causes the trigger to rotate about the mounting pin and disengage from the ratchet allowing the first and second racks to slide along the lateral channel, a first spring operatively connected to the first trigger rod and a second spring operatively connected to the second trigger rod, the first and second springs imparting a laterally biasing force against the first and second trigger rods, respectively, causing the pawl to engage the ratchet.

3. The surgical leg positioner of claim 2, wherein the joint attaching the main rail to the vertical bracket is laterally offset from the main rail axis.

4. The surgical leg positioner of claim 3, further comprising a rail lock assembly attached to the first end and second distal ends.

5. The surgical leg positioner of claim 4, wherein the rail lock assembly comprises:
a. a clamp actuator defining a clamp rod slot, the clamp actuator operatively connected to the first distal end;
b. a clamp rod insertable through the clamp rod slot and slidably connected to the first distal end; and
c. a spring biasing the clamp actuator against the clamp rod to create a resistance that prevents the first distal end of the main rail from moving relative to the second distal end of the fixed rail.

6. The surgical leg positioner of claim 5, wherein the clamp actuator is movable between a first configuration and a second configuration, wherein in the first configuration, the clamp actuator biases against the clamp rod, and in the second configuration, the clamp rod is allowed to slide through the clamp rod slot.

7. The surgical leg positioner of claim 3, further comprising a rail mount operatively attached to the main rail at the first distal end and a foot brace to allow the foot brace to move longitudinally along the main rail.

8. The surgical leg positioner of claim 3, further comprising a horizontal bracket having a medial end and a lateral end, the lateral end rotatably connected to the vertical bracket at the joint defining a joint axis, wherein the horizontal bracket is rotatable about the joint axis, and wherein the medial end is operatively connected to the first proximal end of the main rail to offset the joint axis from the main rail axis.

9. The surgical leg positioner of claim 3, wherein the swing arm module further comprises a base arm to attach the swing arm module to the thigh clamp module, wherein the vertical bracket comprises an upper end and a lower end opposite the upper end, the upper end attached to the base arm at a first joint defining a first joint axis, the vertical bracket configured to rotate about the first joint axis to allow the main rail to move up and down.

10. The surgical leg positioner of claim 9, wherein the vertical bracket comprises a brake to lock the first joint to prevent rotation of the vertical bracket about the first joint axis.

11. The surgical leg positioner of claim 10, wherein the brake is a slide brake and the first joint comprises a toothed gear, wherein the slide brake has a first end, a second end opposite the first end, and a handle therebetween, the first end of the slide brake comprising a wedge configured to engage the toothed-gear to lock the first joint.

12. The surgical leg positioner of claim 2, wherein the surgical bed clamp comprises:
a. a base clamp;
b. a vertical post protruding from the base clamp;
c. a compression plate attached to the vertical post, wherein the compression plate comprises a first plate portion, a second plate portion adjacent to the first plate portion, and a compression lock operatively connected to the first plate portion and the second plate portion to cause the first plate portion and the second plate portion to be compressed together and released; and d. a horizontal post perpendicular to the vertical post and protruding transversely from the compression plate, the horizontal post having a first end, and a second end opposite the first end, wherein the compression plate is mounted adjacent to the first end of the horizontal post and configured to slide along the horizontal post and be clamped along the horizontal post.

13. The surgical leg positioner of claim 2, further comprising a foot brace, wherein the foot brace comprises a plantar portion having a heel end and a toe end opposite the heel end; a heel portion extending substantially perpendicularly from the plantar portion at the heel end; and a rotation lock base, comprising an adjustable handle, and a plurality of gears, wherein the adjustable handle rotates the plurality of gears to rotate the foot brace.

* * * * *